United States Patent
Williams et al.

(10) Patent No.: US 7,271,305 B2
(45) Date of Patent: Sep. 18, 2007

(54) METHOD OF OBTAINING PARA-XYLENE

(75) Inventors: Bryce A. Williams, Lisle, IL (US); Ruth Ann Doyle, Oswego, IL (US); Jeffrey T. Miller, Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 557 days.

(21) Appl. No.: 10/427,515

(22) Filed: May 1, 2003

(65) Prior Publication Data
US 2004/0220439 A1 Nov. 4, 2004

(51) Int. Cl.
C07C 5/27 (2006.01)
C07C 7/12 (2006.01)

(52) U.S. Cl. ............ 585/478; 585/477; 585/820; 585/828

(58) Field of Classification Search ........... 585/478, 585/477, 820, 828
See application file for complete search history.

(56) References Cited

U.S. PATENT DOCUMENTS

| | | | |
|---|---|---|---|
| 2,985,589 A | 5/1961 | Broughton et al. | |
| 3,201,491 A | 8/1965 | Stine et al. | |
| 3,626,020 A | 12/1971 | Neuzil | |
| 3,696,107 A | 10/1972 | Neuzil | |
| 3,699,182 A | 10/1972 | Cattanach | |
| 3,700,589 A | 10/1972 | Symoniak | |
| 3,707,550 A * | 12/1972 | Stine et al. | 585/478 |
| 3,724,170 A * | 4/1973 | Allen et al. | 95/86 |
| 3,729,523 A | 4/1973 | Grandio, Jr. et al. | |
| 4,039,599 A | 8/1977 | Gewartowski | |
| 4,098,836 A | 7/1978 | Dywer | |
| 4,176,053 A | 11/1979 | Holcombe | |
| 4,184,943 A | 1/1980 | Anderson | |
| 4,210,771 A | 7/1980 | Holcombe | |
| 4,372,022 A | 2/1983 | Puckett | |
| 4,374,022 A | 2/1983 | Fuderer | |
| 4,381,419 A | 4/1983 | Wylie | |
| 4,402,832 A | 9/1983 | Gerhold | |
| 4,476,345 A | 10/1984 | Gray, Jr. et al. | |

(Continued)

FOREIGN PATENT DOCUMENTS

CN  1051549  5/1991

(Continued)

OTHER PUBLICATIONS

Ralph T. Yang, "Gas Separation by Adsorption Process," pp. 237-274 (Butterworth Publishers, Boston, 1987) (TP242.Y36).

(Continued)

*Primary Examiner*—Thuan Dinh Dang
(74) *Attorney, Agent, or Firm*—Thomas A. Yassen

(57) ABSTRACT

Disclosed herein is an improved method for making and obtaining para-xylene from a mixture of xylene isomers, and various embodiments of the method. The method generally includes contacting a mixture comprising xylene isomers and ethylbenzene with a para-xylene selective adsorbent to obtain a para-xylene depleted raffinate, and a desorption effluent comprising a para-xylene enriched product. The method also includes isomerizing the para-xylene depleted raffinate. The contacting step is carried out in a manner such that the raffinate need not be pressurized prior to isomerization, thus advantageously obviating expensive compression steps.

70 Claims, 7 Drawing Sheets

U.S. PATENT DOCUMENTS

| | | | |
|---|---|---|---|
| RE31,782 E | 12/1984 | Olson et al. | |
| 4,595,490 A | 6/1986 | Gray, Jr. et al. | |
| 4,705,909 A | 11/1987 | Yan | |
| 4,709,117 A | 11/1987 | Gray, Jr. | |
| 4,886,930 A | 12/1989 | Zinnen | 585/828 |
| 4,899,011 A | 2/1990 | Chu et al. | |
| 4,908,342 A | 3/1990 | McWilliams et al. | |
| 5,011,296 A | 4/1991 | Bartosiak et al. | |
| 5,028,573 A | 7/1991 | Brown et al. | |
| 5,057,643 A | 10/1991 | Zinnen | 585/828 |
| 5,107,062 A | 4/1992 | Zinnen | 585/828 |
| 5,329,060 A | 7/1994 | Swift | |
| 5,367,099 A | 11/1994 | Beck et al. | |
| 5,448,005 A | 9/1995 | Eccli et al. | |
| 5,516,956 A | 5/1996 | Abichandani et al. | |
| 5,866,740 A | 2/1999 | Mikitenko et al. | |
| 5,908,967 A | 6/1999 | Benazzi et al. | |
| 6,111,161 A | 8/2000 | MacPherson et al. | |
| 6,114,592 A | 9/2000 | Gajda et al. | |
| 6,147,272 A | 11/2000 | Mikitenko et al. | |
| 6,150,292 A | 11/2000 | Merlen et al. | |
| 2002/0065444 A1 | 5/2002 | Deckman et al. | |
| 2002/0068844 A1 | 6/2002 | Williams et al. | |
| 2002/0077519 A1 | 6/2002 | Miller et al. | |
| 2002/0099251 A1 | 7/2002 | Doyle et al. | |
| 2002/0107427 A1 | 8/2002 | Doyle et al. | |

FOREIGN PATENT DOCUMENTS

| | | |
|---|---|---|
| CN | 1136549 A | 11/1996 |
| CN | 1404465 | 3/2003 |
| EP | 0138617 | 4/1985 |
| GB | 1420796 | 1/1976 |
| WO | WO 93/17987 | 9/1993 |
| WO | WO 96/22262 | 7/1996 |
| WO | WO 00/69796 | 11/2000 |
| WO | WO 01/62691 | 8/2001 |
| WO | WO 02/04391 | 1/2002 |

OTHER PUBLICATIONS

Sherman (1999) *PNAS* 96:3471-3478.

Bulletin, "ISOMAR™ Process," UOP LLC (1999).

Bulletin, "PAREX™ Process," UOP LLC (1999).

International Preliminary Report on Patentability issued by the International Bureau of WIPO on Nov. 4, 2005, (6 pgs.) in connection with counterpart International Patent Appl. No. PCT/US2004/004981.

English-language translation of First Examination Report (FER) issued by the Indian Patent Office on Dec. 29, 2006, (6 pgs.) in connection with counterpart Indian Patent Appl. No. 1303/MUMNP/2005.

English-language translation of First Office Action issued by the Chinese State Intellectual Property Office on Dec. 29, 2006, (8 pgs.) in connection with counterpart Chinese Patent Appl. No. 200480011664.2.

* cited by examiner

METHOD OF OBTAINING PARA-XYLENE

BACKGROUND OF THE INVENTION

1. Field of the Invention

The invention generally relates to a method of obtaining para-xylene from a feed of $C_8$ aromatics comprising xylene isomers.

2. Brief Description of Related Technology

Hydrocarbon mixtures containing $C_{8+}$ aromatics are by-products of certain oil refinery processes including, but not limited to, catalytic reforming processes. These hydrocarbon mixtures typically contain up to about 30 weight percent (wt. %) $C_{9+}$ aromatics, up to about 10 wt. % non-aromatics, up to about 50 wt. % ethylbenzene, the balance (e.g., up to about 100 wt. %) being a mixture of xylene isomers. Most commonly present among the $C_8$ aromatics are ethylbenzene ("EB"), and xylene isomers, including meta-xylene ("mX"), ortho-xylene ("oX"), and para-xylene ("pX"). Typically, when present among the $C_8$ aromatics, ethylbenzene is present in a concentration of up to about 20 wt. % based on the total weight of the $C_8$ aromatics. The three xylene isomers typically comprise the remainder of the $C_8$ aromatics, and are present at an equilibrium weight ratio of about 1:2:1 (oX:mX:pX). Thus, as used herein, the term "equilibrated mixture of xylene isomers" refers to a mixture containing the isomers in the weight ratio of about 1:2:1 (oX:mX:pX).

Ethylbenzene is useful in making styrene. Meta-xylene is useful in making isophthalic acid, which itself is useful to make specialty polyester fibers, paints, and resins. Ortho-xylene is useful in making phthalic anhydride, which itself is useful to make phthalate-based plasticizers. While meta-xylene and ortho-xylene are useful raw materials, demands for these isomers and materials made therefrom are not as great as the demand for para-xylene and the materials made from para-xylene. Para-xylene is a raw material useful in making terephthalic acids and esters, which are used to make polymers, such as poly(butene terephthalate), poly(ethylene terephthalate), and poly(propylene terephthalate).

Because of their usefulness, efficient separation of ethylbenzene and the various xylene isomers from each other is of particular and continuing interest. Depending upon the concentrations in which each is present in a $C_8$ aromatics mixture, and depending upon the demand of a particular isomer over the others or ethylbenzene or a material made therefrom, separation alone may not be sufficient to obtain adequate quantities of any particular isomer. For example, because there is generally a higher demand for para-xylene compared to its other isomers or ethylbenzene, it is usually more desirable to increase or even maximize para-xylene production from a particular $C_8$ aromatics mixture. Thus, separation of para-xylene oftentimes is coupled with isomerization of meta- and ortho-xylene isomers to the desired para-xylene and, optionally, conversion of the ethylbenzene.

The separation step of para-xylene production processes generally falls into two categories, one of which is crystallization and the other of which is liquid-phase adsorption chromatography. Crystallization was initially developed by Amoco Corporation with subsequent improvements and modifications by Institut Francais du Petrole ("IFP"), Mobil Corporation ("Mobil"), UOP Inc. ("UOP"), and others. As described in more detail below, crystallization has its limits and can be very expensive since crystallization of the various xylene isomers occurs at very low temperatures (e.g., about −70° C. to 0° C.), typically requiring multi-stage refrigeration systems with large gas compressors. Liquid-phase adsorption chromatography, also referred to as simulated moving bed adsorption chromatography ("SiMBAC"), was commercially developed by IFP and UOP. SiMBAC also has its limits and is expensive to operate because it requires a large-volume internal recycle of various hydrocarbon desorbent materials. Additionally, the effluent streams from the adsorption step must be separated from the desirable products in downstream distillation steps. Thus, the foregoing conventional crystallization and liquid-phase adsorption chromatography processes are disadvantageous because of significant capital and energy costs associated with each.

One method of producing para-xylene from a $C_{8+}$ hydrocarbon mixture includes passing the mixture through a separation column to remove heavies, such as $C_{9+}$ hydrocarbons. A lighter, overhead stream from the column, predominantly containing a $C_8$ hydrocarbon mixture comprising the xylene isomers and ethylbenzene, can be resolved in a separation unit. Because ethylbenzene, meta-, ortho-, and para-xylenes have identical molecular weights and have similar boiling points (of about 136° C., about 139° C., about 138° C., and about 144° C., respectively), separation by way of fractional distillation is impractical. An alternative to fractional distillation includes low-temperature crystallization, which exploits the differences in freezing or crystallization temperatures of the various components—para-xylene crystallizes (at about 13.3° C.) before the other xylene isomers (ortho-xylene and meta-xylene crystallize at about −25.2° C. and about −47.9° C., respectively). In the physical system of the three xylene isomers, there are two binary eutectics of importance: the para-xylene/meta-xylene binary eutectic and the para-xylene/ortho-xylene binary eutectic. As para-xylene crystallizes from the mixture, the remaining mixture approaches one of these binary eutectics, depending upon the starting composition of the mixture. Therefore, in commercial-scale processes, para-xylene is crystallized such that the binary eutectics are approached—but not reached—to avoid co-crystallization of the other xylene isomers, which would lower the purity of the obtained para-xylene. Because of these binary eutectics, the amount of para-xylene recoverable per pass through a crystallization process typically is no greater than about 65% of the amount of para-xylene present in the stream fed to the crystallization unit.

Alternatively, certain components of the $C_8$ hydrocarbon mixture may be separated from the mixture prior to any crystallization such as, for example, by liquid phase adsorption (e.g., UOP's PAREX™ process and IFP's ELUXYL™ process) utilizing a faujasite (zeolite) to chromatographically separate para-xylene from $C_8$ mixtures containing para-xylene. The para-xylene lean stream exiting the separation unit typically is pressurized and reacted in the presence of a catalyst to obtain an equilibrated mixture of xylene isomers, which is then recycled to the liquid adsorber. By separating para-xylene from the $C_8$ hydrocarbon mixture prior to crystallization, para-xylene recovery in the crystallization unit can be increased from no greater than about 65% to about 85%, overcoming some of the problems posed by the binary eutectics. See generally Swift (UOP) U.S. Pat. No. 5,329,060.

Another method of producing para-xylene from a $C_8$ hydrocarbon mixture includes passing the mixture, in a gaseous phase, through an adsorption bed containing an adsorbent that is selective for adsorbing para-xylene and ethylbenzene to obtain, after suitable desorption, separate streams, one of which contains predominantly meta- and ortho-xylenes and the other of which contains para-xylene, ethylbenzene, and desorbed feed present in void spaces of the adsorbent. The adsorption is carried out at a temperature between 140° C. and 370° C., a pressure between atmospheric pressure and 300 kilopascals (absolute) (kPa) (about 65 pounds per square inch absolute (psia)), and with the aid of Mobil-5 (MFI) type zeolite molecular sieves, including ZSM-5 (Zeolite Socony Mobil zeolite molecular sieves are commercially available from ExxonMobil Chemicals), ferrierite, and silicalite-1 zeolite molecular sieves, including binder free silicalite-1 zeolite molecular sieves. The desorption of the para-xylene and ethylbenzene can be carried out with a gaseous desorbent containing water at a temperature within the same range of the adsorption, and at a pressure between atmospheric and 1000 kPa (about 145 psia). Alternatively, the desorption can be carried out without a desorbent, by mere depressurization at a pressure between 1 kPa and 4 kPa (about 0.15 psia to about 0.58 psia). In such a method, a substantial amount of feed remains in the voids of the adsorbent, which eventually is removed during the desorption step, but disadvantageously contaminates the desorbed stream containing para-xylene and ethylbenzene. See generally Long et al. (China Petrochemical Company and Fudan University) Chinese Patent Publication No. 1,136,549 A. Others have used ZSM-8 and ZSM-5 (each optionally reacted with silanes) to separate aromatics like xylene isomers and ethylbenzene such as disclosed in, for example, U.S. Pat. Nos. 3,699,182, 3,729,523, and 4,705,909, and British Patent No. 1,420,796.

The foregoing crystallization and SiMBAC steps can be made more attractive if the feedstocks to those steps were re-formulated to contain a higher-than-equilibrium concentration of para-xylene. Such a re-formulation can be carried out by selective toluene disproportionation as described in, for example, International (PCT) Publication Nos. WO 00/69796 and WO 93/17987. Both crystallization and SiMBAC steps also can be designed and operated by those skilled in the art to concentrate para-xylene streams for subsequent purification steps. However, even these steps suffer from many (or all) of the disadvantages discussed above. Another method to produce feedstocks with higher-than-equilibrium para-xylene concentration is by pressure swing adsorption ("PSA") processes. Such processes have been widely practiced for separation of gases such as air into nitrogen and oxygen, water removal from air, and hydrogen purification, and are generally described in Ralph T. Yang, "Gas Separation by Adsorption Processes," pp. 237-274 (Butterworth Publishers, Boston, 1987) (TP242.Y36).

Fewer applications of PSA have been realized for hydrocarbon purifications, particularly purification of hydrocarbons that are liquid under ambient conditions, however. One notable exception is the ISOSIV™ process, developed by the Union Carbide Corporation, which is useful for the separation of straight-chain or normal paraffinic hydrocarbons from branched or iso-paraffinic hydrocarbons. The ISOSIV™ process operates at substantially constant adsorption pressure (i.e., constant total pressure in the adsorption unit during the adsorption step) and uses an inert gas (e.g., hydrogen) to purge, sweep, or otherwise achieve desorption of the adsorbed hydrocarbons from the adsorbent. See U.S. Pat. No. 3,700,589. Over time, the ISOSIV™ process was improved by adding additional adsorption units in the adsorption step, thus permitting recycle of feed to improve the overall purity and recovery of the desired iso-paraffin. See U.S. Pat. No. 4,176,053. The use of multiple adsorption units during the adsorption step, however, has its limits as diminishing returns are realized when too many units are used. See U.S. Pat. Nos. 4,476,345 and 4,595,490 (disclosing the benefits of fewer units and staggered adsorption/desorption cycles). The ISOSIV™ process can be made more attractive if the paraffin mixture fed to the adsorption unit has a higher-than-equilibrium concentration of n-paraffins. Thus, U.S. Pat. No. 4,210,771 discloses an isomerization unit upstream of the adsorption unit to convert iso-paraffins to n-paraffins. In the ISOSIV™ processes utilizing a downstream isomerization reactor (downstream relative to the adsorption unit), it is the adsorbed material that is desorbed and ultimately isomerized—the raffinate from the adsorber bed is not isomerized. Other improvements have been made to the ISOSIV™ process in general. See e.g., U.S. Pat. Nos. 4,372,022 and 4,709,117. Notably, however, no provisions are made in the ISOSIV™ process to separate hydrocarbons other than paraffins.

Clearly ISOSIV™ process effluent streams require capital- and energy-intensive downstream equipment and processing. Moreover, application of the ISOSIV™ process and the associated teachings to the production of para-xylene would present its own problems not adequately addressed in the art. For example, the para-xylene-lean effluent will require expensive pressurization (or re-pressurization) as it is fed to a downstream isomerization unit. As noted above, separation of xylene isomers oftentimes is coupled with isomerization of meta- and ortho-xylenes to the desired para-xylene. Such isomerization is carried out in a high pressure reactor. Even with an understanding of the ISOSIV™ process and an attempted application of the process to produce para-xylene, there is no guidance as to how to introduce the para-xylene depleted raffinate to the isomerization reactor without an expensive pressurization (or repressurization) step between the adsorption unit and the isomerization reactor.

Deckman et al. (Exxon Chemical Company) U.S. Patent Application Publication No. 2002/0065444 A1, for example, discloses a method of making para-xylene from mixed xylenes specifying a PSA or temperature-swing adsorption ("TSA") unit and at least one isomerization reactor. The Deckman publication teaches an isomerization reactor immediately upstream of the PSA unit and no compression step between the reactor and the PSA unit. See FIGS. 1 and 2 of the Deckman publication. Such a teaching implies to one skilled in the art that the reactor operates and reactor effluents exit the reactor at a pressure exceeding the inlet pressure of the PSA unit. The raffinate exits the PSA unit at a high temperature, but reduced pressure (due to depressurization to accomplish desorption), requiring a compressor (or blower) to pressurize the stream before it is recycled to the isomerization reactor. Though not expressly described in the Deckman publication, the raffinate exits the PSA at temperatures too high to make compression practical in a compressor. Thus, the raffinate must be cooled to a suitable temperature before it can be compressed. In cooling the raffinate, certain constituents therein (e.g., xylene isomers) will condense. All of the condensable material must be separated from the uncondensable gas. The condensed material then is heated and pumped into the isomerization reactor, while the now-cooled, uncondensable gas is compressed in a compressor and then sent into the isomerization reactor. Thus, the disclosure in the Deckman publication is somewhat incomplete in that it lacks a specific disclosure of the necessary heat exchanger (condenser), gas/liquid separator, and liquids pump required to pass the PSA raffinate into the isomerization reactor at the appropriate pressure. Notwithstanding, the disclosed method requires a blower or compressor on each of the swing adsorption process effluent streams. As readily understood by those skilled in the art, such blowers and compressors typically are very expensive to purchase and operate, and should be avoided whenever possible.

One might consider operating the swing adsorption unit disclosed in the Deckman publication at a pressure high enough such that the reduced pressure to accomplish desorption remains sufficiently high so as not to require additional pressurization prior to feeding to downstream processing units such as an isomerization reactor. In practice, however, operating the adsorption unit at such a high desorption pressure will disadvantageously and dramatically lower the productivity of the adsorbent.

Thus, while there are various methods of obtaining para-xylene from a $C_8$ aromatic mixtures, these methods are very complex and include necessary and expensive upstream and downstream processing steps.

SUMMARY OF THE INVENTION

Disclosed herein is an improved method for making and obtaining para-xylene from a mixture of xylene isomers. In one embodiment, the method includes contacting at a substantially non-decreasing total pressure a gaseous mixture comprising xylene isomers and ethylbenzene with a para-xylene selective adsorbent to obtain a para-xylene depleted raffinate and a desorption effluent comprising a para-xylene enriched product. The method also includes isomerizing at least a portion of the para-xylene depleted raffinate.

In an alternative embodiment, the method includes contacting at a first pressure a mixture comprising xylene isomers and ethylbenzene with a para-xylene selective adsorbent to obtain a para-xylene depleted raffinate and a desorption effluent comprising a para-xylene enriched product. In this embodiment, the method also includes isomerizing at a second pressure at least a portion of the para-xylene depleted raffinate, wherein the first pressure is equal to or greater than the second pressure.

In another alternative embodiment, the method includes contacting a mixture comprising xylene isomers, ethylbenzene, and a non-adsorbable, non-reactive gas with a para-xylene selective adsorbent to obtain a para-xylene depleted raffinate and a desorption effluent comprising a para-xylene enriched product. In this embodiment, the method also includes isomerizing at least a portion of the para-xylene depleted raffinate. The gas is present in an amount sufficient to ensure a raffinate pressure equal to or greater than an isomerization step pressure, while maintaining the partial pressure of the xylene isomers and ethylbenzene at or below the respective condensation pressures of the xylene isomers and ethylbenzene.

In a further alternative embodiment, the method includes contacting a gaseous mixture comprising xylene isomers and ethylbenzene with a para-xylene selective adsorbent to obtain a para-xylene depleted raffinate and a desorption effluent comprising a para-xylene enriched product. In this embodiment, the method also includes isomerizing at least a portion of the para-xylene depleted raffinate. The sum of the partial pressures of the xylene isomers and ethylbenzene is less than the total pressure of the mixture.

In yet another alternative embodiment, the method includes contacting a xylene isomers mixture and a non-adsorbable gas with a para-xylene selective adsorbent to obtain a para-xylene depleted raffinate comprising hydrocarbons substantially free of para-xylene and a desorption effluent comprising a para-xylene enriched product. The method also includes isomerizing at least a portion of the para-xylene depleted raffinate. The gas is non-reactive with the mixture during the contacting step, and is present in an amount sufficient to provide a gas-to-hydrocarbon mole ratio in the para-xylene depleted raffinate of about 0.1:1 to about 10:1.

Additional features of the invention may become apparent to those skilled in the art from a review of the following detailed description, taken in conjunction with the drawings, the examples, and the appended claims.

BRIEF DESCRIPTION OF THE DRAWINGS

For a more complete understanding of the invention, reference should be made to the following detailed description and accompanying drawings wherein.

Figure 1:
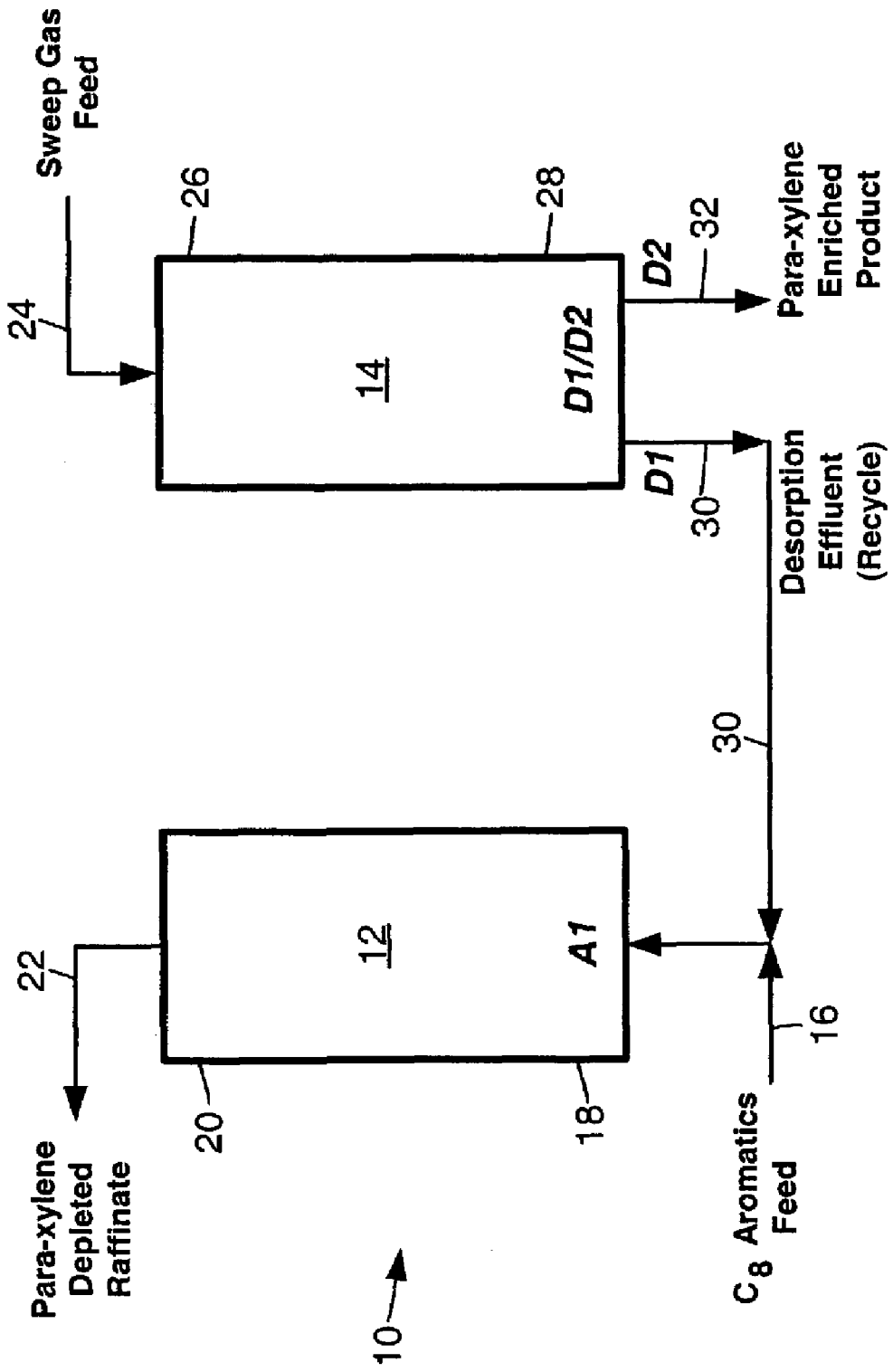
FIG. 1 is a process flow diagram illustrating one cycle of a two-bed partial pressure swing adsorption (PPSA) system suitable for carrying out the disclosed method.

While the disclosed method is susceptible of embodiments in various forms, there are illustrated in the drawings (and will hereafter be described) specific embodiments of the invention, with the understanding that the disclosure is intended to be illustrative, and is not intended to limit the invention to the specific embodiments described and illustrated herein.

DETAILED DESCRIPTION OF THE INVENTION

The invention generally relates to a non-decreasing total pressure/swinging partial pressure method of adsorbing para-xylene from a feed of $C_8$ aromatics comprising xylene isomers, desorbing and collecting an adsorbed para-xylene enriched product, and isomerizing an unadsorbed (para-xylene depleted) portion of the feed to produce a mixture of xylene isomers, which can be combined with the feed.

In one embodiment, the method includes contacting at a substantially non-decreasing total pressure a gaseous mixture comprising xylene isomers and ethylbenzene with a para-xylene selective adsorbent to obtain a para-xylene depleted raffinate and a desorption effluent comprising a para-xylene enriched product. The method also includes isomerizing at least a portion of the para-xylene depleted raffinate, preferably at a pressure that is equal to or less than the substantially non-decreasing total pressure, and more preferably at a pressure that is less than the substantially non-decreasing total pressure. The sum of the partial pressures of the xylene isomers and ethylbenzene preferably is less than the substantially non-decreasing total pressure, and more preferably the sum of the partial pressures is about 15% to about 99.5% of the substantially constant total pressure. More preferably, the sum of the partial pressure is about 35% to about 75% of the substantially constant total pressure, and most preferably the sum is about 45% to about 60% of the substantially constant total pressure. The method also can include separating substantially pure para-xylene from the desorption effluent, preferably at a pressure that is equal to or less than the substantially non-decreasing total pressure, and more preferably at a pressure that is less than the substantially non-decreasing total pressure.

In this embodiment, the method also can include combining with the mixture a non-adsorbable gas that is non-reactive with the mixture during the contacting step. Preferably the gas is present in an amount sufficient to provide a gas-to-hydrocarbon mole ratio in the para-xylene depleted raffinate of about 0.1:1 to about 10:1. Alternatively, or additionally, the gas is present in an amount sufficient to ensure that the substantially non-decreasing total pressure is equal to or greater than an isomerization step pressure, while maintaining the partial pressure of the xylene isomers and ethylbenzene at or below the respective condensation pressures of the xylene isomers and ethylbenzene. Preferably, the gas is present in an amount sufficient to ensure that the substantially non-decreasing total pressure is greater than the isomerization step pressure. Still further, the gas preferably is present in an amount sufficient to avoid condensation of the xylene isomers.

In an alternative embodiment, the method includes contacting at a first pressure a mixture (preferably a gaseous mixture) comprising xylene isomers and ethylbenzene with a para-xylene selective adsorbent to obtain a para-xylene depleted raffinate and a desorption effluent comprising a para-xylene enriched product. The method also includes isomerizing at a second pressure at least a portion of the para-xylene depleted raffinate, wherein the first pressure is equal to or greater than the second pressure, and preferably wherein the first pressure is greater than the second pressure. The sum of the partial pressures of the xylene isomers and ethylbenzene preferably is less than the first pressure, and more preferably it is about 15% to about 99.5% of the first pressure. Preferably, the first pressure is a substantially non-decreasing pressure. The method also can include separating substantially pure para-xylene from the desorption effluent, preferably at a pressure that is equal to or less than the first pressure, and more preferably at a pressure that is less than the first pressure.

In this embodiment, the method also can include combining with the mixture a non-adsorbable gas that is non-reactive with the mixture during the contacting step. Preferably the gas is present in an amount sufficient to provide a gas-to-hydrocarbon mole ratio in the para-xylene depleted raffinate of about 0.1:1 to about 10:1. Alternatively, or additionally, the gas is present in an amount sufficient to maintain the partial pressure of the xylene isomers and ethylbenzene at or below the respective condensation pressures of the xylene isomers and ethylbenzene. Preferably, the gas is present in an amount sufficient to avoid condensation of the xylene isomers.

In another alternative embodiment, the method includes contacting a mixture (preferably a gaseous mixture) comprising xylene isomers, ethylbenzene, and a non-adsorbable, non-reactive gas with a para-xylene selective adsorbent to obtain a para-xylene depleted raffinate and a desorption effluent comprising a para-xylene enriched product, and isomerizing at least a portion of the para-xylene depleted raffinate. The gas is present in an amount sufficient to ensure a raffinate pressure equal to or greater than an isomerization step pressure, while maintaining a the partial pressure of the xylene isomers and ethylbenzene at or below the respective condensation pressures of the xylene isomers and ethylbenzene. Alternatively, or additionally, the gas preferably is present in an amount sufficient to ensure a raffinate pressure greater than the isomerization step pressure, more preferably the gas is present in an amount sufficient to avoid condensation of the xylene isomers.

In this embodiment of the method, the contacting step preferably is carried out at a substantially non-decreasing total pressure. The method also can include separating substantially pure para-xylene from the desorption effluent, preferably at a pressure that is equal to or less than the substantially non-decreasing total pressure, and more preferably at a pressure that is less than the substantially non-decreasing total pressure.

In a further alternative embodiment, the method includes contacting a gaseous mixture comprising xylene isomers and ethylbenzene with a para-xylene selective adsorbent to obtain a para-xylene depleted raffinate and a desorption effluent comprising a para-xylene enriched product, and isomerizing at least a portion of the para-xylene depleted raffinate. In this embodiment, the sum of the partial pressures of the xylene isomers and ethylbenzene is less than the total pressure of the mixture, and preferably it is about 15% to about 99.5% of the total pressure. The total pressure preferably is substantially non-decreasing. The para-xylene depleted raffinate is isomerized preferably at a pressure that is equal to or less than the total pressure, and more preferably at a pressure that is less than the total pressure. The method also can include separating substantially pure para-xylene from the desorption effluent, preferably at a pressure that is equal to or less than the total pressure, and more preferably at a pressure that is less than the total pressure.

In this embodiment, the method also can include combining with the mixture a non-adsorbable gas that is non-reactive with the mixture during the contacting step. Preferably the gas is present in an amount sufficient to ensure that the total pressure is equal to or greater than an isomerization step pressure, while maintaining the partial pressure of the xylene isomers and ethylbenzene at or below the respective condensation pressures of the xylene isomers and ethylbenzene. Preferably, the gas is present in an amount sufficient to ensure that the total pressure is greater than the isomerization step pressure. Alternatively, or additionally, the gas preferably is present in an amount sufficient to avoid condensation of the xylene isomers.

In yet another alternative embodiment, the method includes contacting a xylene isomers mixture (preferably a gaseous mixture) and a non-adsorbable gas with a para-xylene selective adsorbent to obtain a para-xylene depleted raffinate comprising hydrocarbons substantially free of para-xylene and a desorption effluent comprising a para-xylene enriched product, and isomerizing at least a portion of the para-xylene depleted raffinate. In this embodiment, the gas is non-reactive with the mixture during the contacting step, and the gas is present in an amount sufficient to provide a gas-to-hydrocarbon mole ratio in the para-xylene depleted raffinate of about 0.1:1 to about 10:1. The gas preferably is present in an amount sufficient to ensure a raffinate pressure equal to or greater than an isomerization step pressure, while maintaining the partial pressure of the xylene isomers and ethylbenzene at or below the respective condensation pressures of the xylene isomers and ethylbenzene. Alternatively, or additionally, the gas is present in an amount sufficient to ensure a raffinate pressure greater than the isomerization pressure, and more preferably the gas is present in an amount sufficient to avoid condensation of the xylene isomers.

In this embodiment of the method, the contacting step preferably is carried out at a substantially non-decreasing pressure. Additionally, the method can include separating substantially pure para-xylene from the desorption effluent, preferably at a pressure that is equal to or less than the substantially non-decreasing pressure, and more preferably at a pressure that is less than the substantially non-decreasing pressure.

The non-adsorbable gas referred to above can be one having molecular dimensions sufficiently small to enter intracrystalline cavities of the molecular sieve (adsorbent), but it need not have such dimensions. The non-adsorbable gas preferably is one that is not strongly enough adsorbed to the adsorbent to displace the hydrocarbons adsorbed thereon to any significant degree. Suitable non-adsorbable gases include, but are not limited to, argon, carbon dioxide, helium, hydrogen, nitrogen, and light paraffins, such as methane, ethane, propane, butane, and mixtures thereof. Preferably, however, the non-adsorbable gas is one or more materials selected from the group consisting of hydrogen, nitrogen, and light paraffins. More preferably the non-adsorbable gas is hydrogen. Notwithstanding the foregoing, the non-adsorbable gas may include trace amounts of contaminants, such as benzene, toluene, $C_9$ paraffins and naphthenes, and $C_{8+}$ aromatics. The gas can be combined with the mixture (fed to the adsorbent) to increase the purity and yield of the para-xylene. Preferably, the gas is present in an amount sufficient to provide a gas-to-hydrocarbon mole ratio in the para-xylene depleted raffinate of about 0.1:1 to about 10:1. Understanding that the non-adsorbable gas can include hydrocarbons (e.g., light paraffins), reference to "hydrocarbon" in the term "gas-to-hydrocarbon mole ratio" refers to hydrocarbons other than those that might be part of the non-adsorbable gas. Alternatively, or additionally, the gas is present in an amount sufficient to ensure that the pressure at which the contacting step is carried out is equal to or greater than the pressure at which isomerization step is carried out. The gas also is referred to herein as a "sweep" gas.

As noted above, the non-adsorbable gas, combinable with a fresh feed mixture of $C_8$ aromatics fed to the adsorbent bed, should be present in amounts sufficient to ensure a pressure gradient between the contents of and streams exiting the bed and downstream operations (e.g., isomerization, condensation, etc.). Additionally, and in certain preferred embodiments, the gas is present in an amount sufficient to maintain the partial pressure of the xylene isomers and ethylbenzene at or below the respective condensation pressures of the xylene isomers and ethylbenzene. Alternatively, or additionally, the gas is present in an amount sufficient to avoid condensation of the xylene isomers. The presence of this gas during the contacting step permits para-xylene selective adsorption to occur under higher pressure than presently possible utilizing simple pressure-swing adsorption. Specifically, the presence of the gas permits a higher total pressure within the adsorber bed, while advantageously maintaining the partial pressure of the xylene isomers constant (and not appreciably greater than that experienced in simple pressure-swing adsorption). In the absence of the gas, the bed cannot be operated at such high total pressure without also, disadvantageously, resulting in condensation of the xylene isomers. Thus, the presence of the gas advantageously permits the higher total pressure within the bed without the detrimental onset of xylene condensation within the bed. Without the gas, operation of the bed at the high total pressure would require a concomitant increase in temperature to maintain the xylene isomers in the gas state. Such higher temperatures, however, would compromise the para-xylene selectivity of the adsorbent—higher amounts of the other isomers would also be adsorbed thus compromising the para-xylene purity. Thus, the higher total pressure in the bed obtainable by the presence of the gas does not disadvantageously affect the selectivity of the adsorbent because the partial pressures of the xylene isomers does not appreciably change.

The term "raffinate" as used herein is intended to refer to that portion of a fluid (gas or liquid) that remains after other desired components have been removed by, for example, adsorption. The para-xylene depleted raffinate generally will include one or more of the constituents of the mixture (the feed) contacting the adsorbent, but a lower para-xylene concentration than that of the feed. The term "para-xylene depleted" when used in the phrase "para-xylene depleted raffinate" merely means that the concentration of para-xylene in the raffinate is lower, preferably substantially lower, than the concentration of para-xylene present in the mixture contacting the adsorbent. The term does not mean that the raffinate contains no para-xylene. Thus, the para-xylene depleted raffinate likely will contain a lower concentration of para-xylene, higher concentrations of xylene isomers other than para-xylene, ethylbenzene, and other non-$C_8$ aromatics that may have been present in the feed.

Generally, the para-xylene depleted raffinate will include hydrocarbons substantially free of para-xylene (e.g., meta-xylene, ortho-xylene, toluene, $C_{9+}$ aromatics, and $C_9$ paraffins and naphthenes). Because a non-adsorbable gas non-reactive with the mixture may be combined with the mixture (fed to the adsorbent), the para-xylene depleted raffinate also can include the non-adsorbable gas. Thus, the para-xylene depleted raffinate can include one or more materials selected from the group consisting of argon, carbon dioxide, helium, hydrogen, nitrogen, and light paraffins, such as methane, ethane, propane, butane, and mixtures thereof. The para-xylene depleted raffinate preferably includes hydrocarbons substantially free of para-xylene, and more preferably it includes meta-xylene, ortho-xylene, and hydrogen. Preferably, the para-xylene depleted raffinate will contain ortho-xylene and meta-xylene with less than a total of 25 mole percent of para-xylene and ethylbenzene based on total $C_8$ aromatics present in the raffinate, and more preferably less than ten mole percent of para-xylene and ethylbenzene based on total $C_8$ aromatics present in the raffinate, and most preferably less than five mole percent of para-xylene and ethylbenzene based on total $C_8$ aromatics present in the raffinate.

Any portion of the raffinate not isomerized can be passed to other downstream unit operations to purify the meta-xylene and/or ortho-xylene present in the raffinate. As noted above, the method includes isomerizing at least a portion of the para-xylene depleted raffinate. Preferably, the isomerization is carried out to obtain a hydrocarbon mixture comprising equilibrated xylene isomers. To increase the purity and yield of para-xylene, a portion (or all) of the xylene isomers obtained by way of isomerization can be combined with the mixture contacting the adsorbent (i.e., recycled). The isomerization step is described in more detail below.

Subsumed in the disclosed method (and the various embodiments thereof) is an understanding by those skilled in the art of suitable processing equipment and controls necessary to carry out the method. Such processing operations equipment (e.g., reactor vessels with appropriate inlets and outlets, heat exchangers, separation units, etc.), associated process control equipment, and quality control equipment, if any. Any other processing equipment, especially where particularly preferred, is specified herein.

Adsorbents most useful in the method generally comprise a non-acidic, molecular sieve and a binder. The molecular sieve should be capable of selectively adsorbing para-xylene within cavities, channels, and pores of the sieve while not adsorbing meta- and ortho-xylenes and non-$C_8$ aromatics (i.e., total exclusion of meta- and ortho-xylenes or having much slower adsorption rates compared to para-xylene). Among the suitable sieves for use herein are those that selectively adsorb not only para-xylene, but also ethylbenzene, since ethylbenzene has a molecular size and structure/shape similar to that of para-xylene. Suitable sieves that selectively adsorb only para-xylene are most preferred. The adsorbents should be non-reactive with the $C_8$ aromatics, and should not possess catalytic reactivity (e.g., isomerization or conversion activity) relative to the $C_8$ aromatics. An adsorbent that is not catalytically reactive typically will exhibit less than ten percent conversion of para-xylene to meta-xylene or ortho-xylene, preferably less than five percent conversion, and more preferably less than one percent conversion, at temperatures encountered during the contacting step of the method. Accordingly, the adsorbents should be non-acidic and, preferably, highly non-acidic.

In general, molecular sieves are ordered, porous crystalline materials. More specifically, molecular sieves typically are formed from silica, alumina, and phosphorus oxide ($PO_4$) tetrahedra that contain a crystalline structure with cavities and/or pores interconnected by channels. The cavities, pores, and channels typically are uniform in size and permit selective separation of hydrocarbons based upon certain molecular characteristics—most commonly, separation by molecular size or shape. Generally, the term "molecular sieve" includes various natural and synthetic crystalline porous materials typically based upon silica tetrahedra in combination with other tetrahedral oxide materials, such as aluminum, boron, gallium, iron, titanium, and the like. In such structures, networks of silicon and elements, such as aluminum are cross-linked through the sharing of oxygen atoms. Substitution of elements, such as aluminum, for silicon in the molecular sieve structure imparts a negative charge to the structure (or overall framework), which should be balanced with positive ions, such as alkali metals, alkaline earth metals, or ammonium, to ensure that the sieve is non-acidic.

The binder preferably is selected from the group consisting of alumina, aluminum phosphate, clay, silica, silica-alumina, silica-alumina-magnesia, silica-alumina-thoria, silica-alumina-zirconia, silica-beryllia, silica-magnesia, silica-magnesia-zirconia, silica-thoria, silica-titania, silica-zirconia, titania, zirconia, and mixtures thereof.

The para-xylene-selective adsorbent should be capable of adsorbing para-xylene preferentially over meta-xylene and ortho-xylene when subjected to an equimolar mixture of xylenes in the vapor (or gas) phase at 50° C., such that the total para-xylene in a desorption effluent of the method is at least about 75 percent on a molar basis (%) relative to the total amount of $C_8$ aromatics present in the desorption effluent, preferably at least about 80%, more preferably at least about 85%, more highly preferably at least about 90%, even more preferably at least about 95%, and most preferably at least about 97%, relative to the total amount of $C_8$ aromatics present in the desorption effluent. The preferential selectivity of suitable adsorbents should be similar or better when subjected to an equilibrated mixture of xylene isomers or a greater-than-equimolar ratio of para-xylene relative to meta-xylene and ortho-xylene. Adsorbent capacity typically is defined as grams adsorbate (i.e., material adsorbed) divided by grams adsorbent, and also can be expressed as a weight percent by multiplying by 100. Thus, in accordance with the various embodiments of the disclosed method, preferably at least about 0.01 grams of para-xylene will be adsorbed per gram of adsorbent. More preferably at least about 0.015 grams of para-xylene will be adsorbed per gram of adsorbent, even more preferably at least about 0.02 grams of para-xylene will be adsorbed per gram of adsorbent, and most preferably at least about 0.03 grams of para-xylene will be adsorbed per gram of adsorbent.

In each of the foregoing embodiments, the desorption effluent preferably contains at least about 50 percent on a molar basis (%) of the para-xylene present in the (feed) mixture, more preferably at least about 75% of the para-xylene present in the mixture, even more preferably at least about 90% of the para-xylene present in the mixture, and most preferably at least about 95% of the para-xylene present in the mixture. Reference herein to the term "para-xylene enriched product" means a product comprising para-xylene with less than a total of 25 mole percent meta-xylene and ortho-xylene based on total $C_8$ aromatics present in the product. Preferably, a para-xylene enriched product has less than ten mole percent meta-xylene and ortho-xylene based on total $C_8$ aromatics present in the product, and more preferably, the product has less than five mole percent meta-xylene and ortho-xylene based on total $C_8$ aromatics present in the product.

The adsorbent can be contained in one or more containers or vessels (also referred to herein as adsorption columns or beds) in which separation of a substantially pure stream of para-xylene and ethylbenzene from a mixture of xylene isomers and ethylbenzene is possible using controlled (or programmed) flow into and out of the containers or vessels. The separation of components taking place in the bed is a modified partial pressure swing adsorption ("PPSA") separation wherein the cycle time is defined as the interval of time starting when a feed mixture is admitted into the bed and ending when the bed is ready for the next addition of feed. Therefore, the "cycle time" can be described as the time interval at which feed is introduced to the bed, e.g., every 30 seconds, every one minute, every five minutes, every ten minutes, every fifteen minutes, etc. The "cycle" is the complete PPSA (i.e., summation of all of the stages). As described in more detail below, the stages are usually discrete steps of the PPSA, such as an adsorption stage (Ax) and various desorption stages (Dx), wherein x is an integer equal to or greater than one.

The contacting step should be carried out under conditions (e.g., temperature and pressure) effective to ensure that the various feed, effluent, and raffinate streams are in a gas/vapor state—and not in a liquid state. Thus, for example, the pressure should be maintained such that gas/vapor streams do not condense. Generally, this can be satisfied by maintaining the pressure at less than about 80% of the critical pressure of the highest boiling key component of the streams or less than about 60% of the dew point pressure of the streams at the various process temperatures, whichever is the lower value. As noted above, the presence of a non-adsorbable gas during the contacting step can help to ensure that, at the very least, the xylene isomers do not condense during the contacting step.

The contacting step preferably should be carried out at an isothermal operating temperature of at least about 175° C., and more preferably at least about 200° C. The isothermal operating temperature during the contacting step preferably should be in a range of about 175° C. to about 400° C., and more preferably about 200° C. to about 300° C. The contacting step also should be carried out at an isobaric operating pressure preferably of at least about 345 kPa (about 50 psia), and more preferably at least about 448 kPa (about 65 psia). The isobaric operating pressure during the contacting step should be in a range of about 345 kPa to about 6895 kPa (about 50 psia to about 1000 psia), preferably about 345 kPa to about 3000 kPa (about 50 psia to about 435 psia), more preferably about 448 kPa to about 3000 kPa (about 65 psia to about 435 psia), and most preferably about 448 kPa to about 2068 kPa (about 65 psia to about 300 psia).

As the term "isothermal" implies, the operating temperature during each of the adsorption and desorption stages of the contacting step should be maintained substantially constant. Reference to the term "substantially constant" as used in the phrase "substantially constant total temperature" means that, during the associated stage, there is no appreciable change in temperature of the bed. In view of the teachings herein, those skilled in the art will recognize that there may be some slight variation in temperature due to changes in flows and/or due to heats of adsorption and desorption. Thus, a stream may exist at the beginning of a stage (adsorption or desorption) at a temperature that is about 85% to about 115% of that temperature at the end of the same stage. Additionally, the temperature of the adsorber feed, adsorber raffinate, adsorber effluent and sweep gas (if any) streams, preferably remains the same as the operating temperature of the bed throughout the stage of the contacting step in which the streams exist.

As the term "isobaric" implies, the operating pressure during each of the adsorption and desorption stages of the contacting step should be maintained substantially constant. Reference to the term "substantially constant" in the phrase "substantially constant total pressure" means that, during the associated stage, there is no appreciable depressurization of the bed. In view of the teachings herein, those skilled in the art will recognize that there may be some slight variation in pressure due to changes in flows or that the partial pressure of an adsorbed or desorbed component will change during the contacting step. Thus, a stream may exist at the beginning of a stage (adsorption or desorption) at a pressure that is about 95% to about 105% of that pressure at the end of the same stage. Additionally, the pressure of the adsorber feed, adsorber raffinate, adsorber effluent and sweep gas (if any) streams, preferably remains the same as the operating pressure of the bed throughout the stage of the contacting step in which the streams exist. Partial pressure of the various components within each stream will, however, change depending upon the temporal disposition of the components within the contacting step—hence the "partial pressure" swing adsorption nature of the method.

In certain embodiments of the method, the contacting step is carried out at a "substantially non-decreasing total pressure," meaning that the successive desorption stages should be carried out at pressures that exceed or substantially equal the pressure of the preceding adsorption stage. Thus, while each stage of the contacting step can be carried out at separate isobaric pressures, the isobaric pressure of a successive desorption stage should not be less than the isobaric pressure of the preceding desorption and adsorption stages. Such an operating parameter advantageously permits recycle of selected cuts of desorption effluents (as described in more detail below) to a bed operating in the adsorption stage, and combination with a fresh $C_8$ aromatics feed, without requiring expensive pumps and compressors to re-pressurize the effluent to the pressure of the fresh $C_8$ aromatics feed or the adsorption stage pressure. The higher pressure in the desorption effluent (higher relative to the adsorption stage pressure) advantageously obviates the need for pumps and compressors to convey the effluent to other downstream processing equipment. Additionally, the higher pressure in the desorption effluent (higher relative to the adsorption stage pressure) facilitates the removal of lighter hydrocarbons therefrom, as such hydrocarbons will likely condense more easily at the higher pressures at which separation of $C_8$ aromatics from the non-adsorbing gas occurs, and minimizes the compression needed to recycle the non-adsorbing gas back to the adsorption unit. Still further, a benefit of the method thus resides in the design that the raffinate obtained from the contacting step does not need to be pressurized prior to downstream isomerization. Because, among other things, the disclosed method obviates expensive compression equipment, it is distinguishable from the ISOSIV™ process and the processes disclosed in Deckman et al. (Exxon Chemical Company) U.S. Patent Application Publication No. 2002/0065444 A1 and Long et al. (China Petrochemical Company and Fudan University) Chinese Patent Publication No. 1,136,549 A.

As noted above, the method includes isomerizing the para-xylene depleted raffinate. Preferably, and as previously noted herein, the isomerization is carried out to obtain a hydrocarbon mixture comprising equilibrated xylene isomers. The isomerization can be carried out in any suitable reactor such as, for example, those described in U.S. Pat. Nos. 4,899,011 and 4,236,996, the disclosures of which are incorporated herein by reference. The reactor should contain a catalyst suitable for carrying out the desired isomerization. Depending upon the type of isomerization desired, different catalysts may be used. For example, certain catalysts are more suited to equilibrate the para-xylene depleted raffinate to the xylene isomers (or to the four predominant $C_8$ aromatics, including ethylbenzene) in concentrations driven by thermodynamics under the isomerization conditions. Such catalysts include, but are not limited to, those disclosed in European Patent No. 138,617, U.S. Pat. Nos. 4,098,836, 4,899,011, 5,011,296, and Re 31,782, the disclosures of which are incorporated herein by reference. Commercially-available catalysts include, but are not limited to, IFPP/Engelhard Octafining and Octafining II catalysts.

Other catalysts are more suited to converting any ethylbenzene present in the raffinate and producing benzene and ethane, as byproducts of the removal. Conversion of ethylbenzene can occur by any catalyst system for ethylbenzene dealkylation, hydrodeethylation, or hydroisomerization. Such catalysts include, but are not limited to, those disclosed in U.S. Pat. No. 4,899,011 (hydrodeethylation), U.S. Pat. No. 4,908,342 (dealkylation), U.S. Pat. No. 5,028,573 (hydroisomerization), U.S. Pat. No. 5,367,099 (hydrodeethylation), U.S. Pat. No. 5,908,967 (hydroisomerization), U.S. Pat. No. 6,150,292 (hydroisomerization), and Re 31,782 (dealkylation), the disclosures of which are incorporated herein by reference. Commercially-available catalysts include, but are not limited to, Mobil High Temperature Isomerization (MHTI) catalysts and Mobil High Activity Isomerization (MHAI) catalysts both of which are commercially available from ExxonMobil Chemicals, and UOP's ISOMAR™ I-9, I-100, I-210, and I-300 catalysts. The para-xylene depleted raffinate can be passed into an isomerization unit divided into multiple zones (or reactors), each zone containing a different catalyst, to carry out a different isomerization reaction corresponding to the catalyst disposed therein. Alternatively, the isomerization can contain only one zone (or reactor) with a single catalyst.

The isomerization can be carried out under various effective conditions that include a wide temperature range. It is generally understood that the para-xylene concentration in an equilibrated mixture of xylenes is not strongly temperature dependent within a temperature range of about 200° C. to about 550° C. Thus, the selection of a particular temperature within the range for a particular isomerization zone (or reactor) should not have a significant impact on the concentration of para-xylene present in the mixture. The selection of a particular isomerization reaction temperature in a particular zone (or reactor) of the isomerization unit of the method, does depend upon many factors, such as whether there is ethylbenzene present in the feed to the unit, whether there is a desire or need to convert the ethylbenzene during isomerization, whether there are two or more isomerization zones (or reactors) operating in series, the temperature of the feed, and combinations of these factors.

Generally, the temperature range for the isomerization step is in a range of about 200° C. to about 550° C., preferably about 250° C. to about 500° C., and more preferably about 340° C. to about 430° C. Conversion of ethylbenzene does not occur to any significant extent at temperatures less than about 300° C. Thus, if conversion of ethylbenzene is desired, then the isomerization should be carried out at a temperature, within the aforementioned temperature ranges, higher than about 300° C. Conversely, if conversion of ethylbenzene is not desired, then the isomerization should be carried out at a temperature, within the aforementioned temperature ranges, lower than about 300° C. If an isomerization unit having multiple zones (or reactors) is being used, it is preferable to maintain a first zone (or reactor) at a temperature, within the aforementioned temperature ranges, higher than about 300° C., and the second zone (or reactor) at a temperature, within the aforementioned ranges, lower than about 300° C.

Of course, without the need to convert ethylbenzene, the lower temperatures provide the method with the benefit of lower energy consumption and lower xylene loss to by-products. Though ethylbenzene serves a useful purpose as a precursor to the formation of styrene, when present in minor quantities, it might not be economical to recover those quantities. Thus, it may be more economical to carry out the isomerization step at high temperatures converting whatever ethylbenzene is present, as opposed to recovering the ethylbenzene. By-products of the isomerization can include $C_{9+}$ hydrocarbons, for example.

The isomerization step preferably is carried out at a pressure equal to or less than the pressure at which the raffinate is obtained from the upstream contacting step and, preferably, at a pressure customary for conventional isomerization reactors. See generally, U.S. Pat. No. 5,516,956 for typical xylene isomerization conditions. Specifically, the total pressure in the isomerization unit, including all hydrocarbons and any other gases that may be present therein, is in a range of about atmospheric pressure to about 6895 kPa (about 1000 psia), preferably about 345 kPa to about 2757 kPa (about 50 psia to about 400 psia), and more preferably about 413 kPa to about 1516 kPa (about 60 psia to about 220 psia).

Referring now to the drawing figures, wherein like reference numbers refer to the identical or similar elements in the various figures, FIG. 1 shows one cycle of a two-bed partial pressure swing adsorption (PPSA) system 10 suitable for carrying out the disclosed method and, specifically, the contacting step therein. As shown, the system 10 includes two identical separation beds—"identical" in that each includes an adsorbent (not shown) and identical inlets and outlets, even though only certain inlets and outlets of each are shown and expressly described herein for purposes of more clearly illustrating the single cycle. The beds are shown arranged in series, wherein a first bed 12 is operating in an adsorption stage ("A1") and the second bed 14 is operating in one of two desorption stages ("D1" and "D2"). When the first bed 12 is adsorbing (A1), the second bed 14 is desorbing in one of the two desorption stages (D1 or D2) and, accordingly, when the second bed 14 is adsorbing, the first bed 12 is in one of the two desorption stages. Additional reference can be made to the following Table I:

TABLE I

| | Bed | |
|---|---|---|
| | First (12) | Second (14) |
| Stage | A1 | D1 |
| Stage | A1 | D2 |
| Stage | D1 | A1 |
| Stage | D2 | A1 |

With continued reference to FIG. 1, a feed mixture comprising xylene isomers and ethylbenzene (also referred to herein as a "$C_8$ aromatics" or "hydrocarbon" feed) is fed via an inlet line 16 to a bottom portion 18 of the first bed 12, and contacted therein with a para-xylene selective adsorbent under the aforementioned conditions (e.g., temperature, pressure, etc.). Upon such contact, para-xylene and ethylbenzene present in the mixture are adsorbed by the adsorbent while other components of the mixture are not adsorbed and are eventually displaced (by incoming feed) from a top portion 20 of the first bed 12 via an outlet line 22 as a para-xylene depleted raffinate. The raffinate can be heated, if necessary, and passed directly to a downstream isomerization unit to obtain an equilibrated mixture of xylene isomers combinable with the $C_8$ aromatics feed.

As shown, while the first bed 12 is adsorbing (A1), the second bed 14 undergoes desorption in successive desorption stages D1 and D2. Specifically, during desorption stage D1, sweep gas is fed via an inlet line 24 to a top portion 26 of the second bed 14, effectively sweeping out through a bottom portion 28 of the second bed 14 an effluent containing the sweep gas, unadsorbed hydrocarbons, and other gas present in void spaces of the adsorbent and second bed 14. The effluent from the D1 desorption stage exits the second bed 14 via an outlet line 30, the effluent primarily containing the sweep gas and hydrocarbons with a composition similar to that of the feed mixture (or slightly enriched in para-xylene and ethylbenzene). Portions of the effluent in outlet line 30 can be combined with fresh mixture fed to the beds (e.g., via inlet line 16 of the first bed 12) to form the converged feed mixture for the adsorption stage (A1).

As in the D1 desorption stage, during the successive D2 desorption stage, sweep gas is continuously fed via the inlet line 24 to the top portion 26 of the second bed 14, effectively sweeping out through the bottom portion 28 of the second bed 14 any hydrocarbons and other gas present in void spaces of the adsorbent and second bed 14 and adhering to the adsorbent. The desorption effluent from the D2 desorption stage exits the second bed 14 via an outlet line 32. Unlike the hydrocarbons in the effluent obtained from the D1 desorption stage, however, the hydrocarbons present in the effluent obtained from the D2 desorption stage are rich in para-xylene and ethylbenzene—substantially higher purity than that of the feed. The D2 desorption effluent primarily contains the product, which can be passed to suitable downstream processes to further process or purify the product into its constituent parts, namely para-xylene and ethylbenzene. The duration of the desorption stages, in the aggregate, equals the duration of the adsorption stage. The duration of the various desorption stages can be adjusted accordingly depending upon the feed provided to the bed, and the yield and purity desired of the product.

Figure 2:
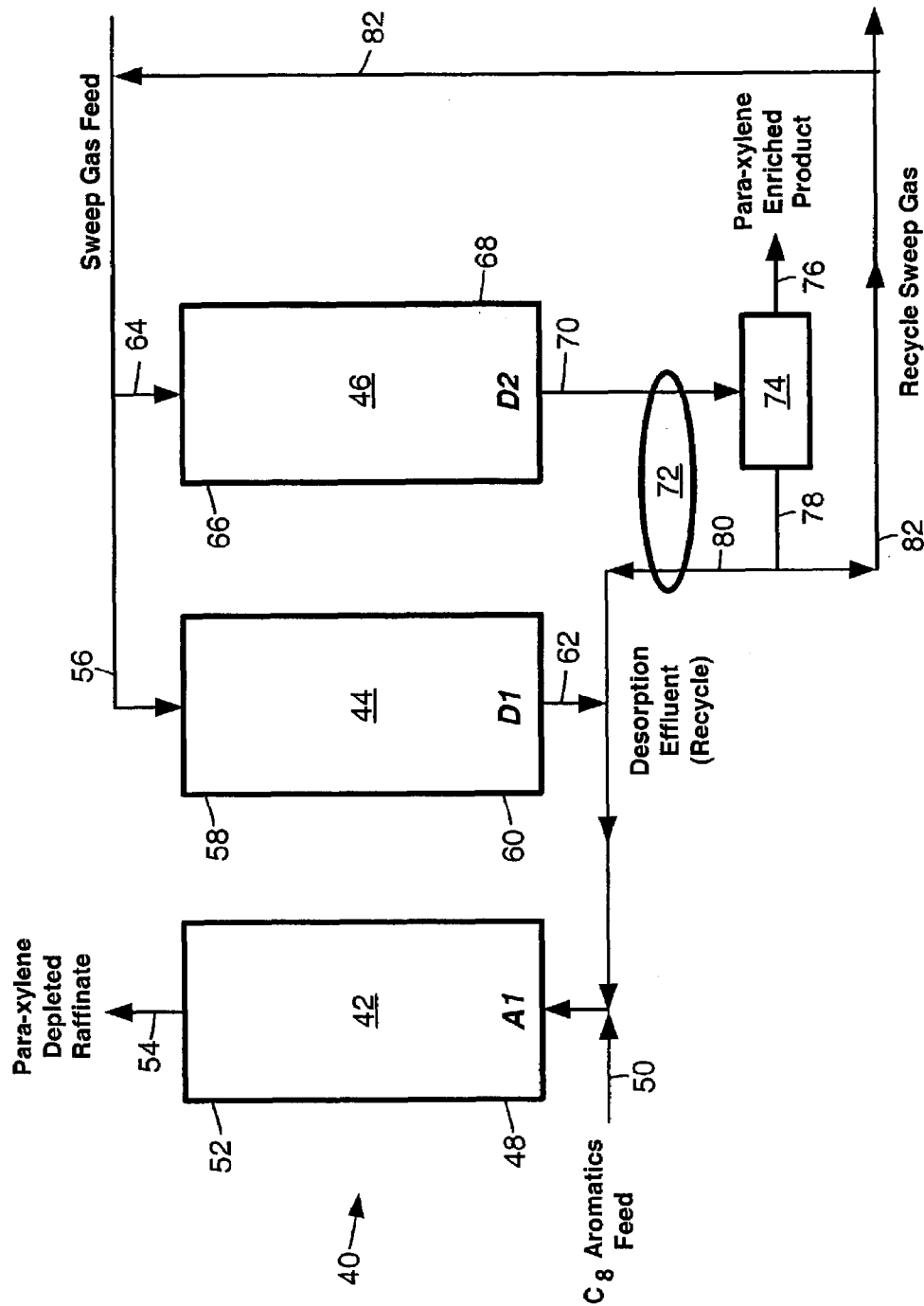
FIG. 2 is a process flow diagram illustrating one cycle of a three-bed PPSA system suitable for carrying out the disclosed method.

Shown in FIG. 2 is a three-bed PPSA system 40 suitable for carrying out the disclosed method and, specifically, the contacting step therein. As shown, the system 40 includes three identical separation beds 42, 44, and 46—"identical" in that each includes an adsorbent (not shown) and identical inlets and outlets, even though only certain inlets and outlets of each are shown and expressly described herein for purposes of more clearly illustrating a single cycle. Additional reference can be made to the following Table II:

TABLE II

|       | Bed       |            |           |
|-------|-----------|------------|-----------|
|       | First (42) | Second (44) | Third (46) |
| Stage | A1        | D1         | D2        |
| Stage | D1        | D2         | A1        |
| Stage | D2        | A1         | D1        |

As indicated in Table II and in FIG. 2, when the first bed 42 is adsorbing (A1), the second and third beds 44 and 46, respectively, are operating in desorption stages D1 and D2, respectively. Similarly, when the third bed 46 is adsorbing (A1), the first and second beds 42 and 44, respectively, are operating in desorption stages D1 and D2, respectively. When the second bed 44 is adsorbing (A1), the third and first beds 46 and 42, respectively, are operating in desorption stages D1 and D2, respectively.

With the first bed 42 serving as a point of reference for the beginning of an on-going, three-part cycle, in the first part, a $C_8$ aromatics feed is introduced to a lower portion 48 of the first bed 42 through an inlet line 50 over a time period (A1) during which the second bed 44 undergoes the D1 desorption stage and the third bed 46 undergoes the D2 desorption stage. Within the first bed 42, the $C_8$ aromatics feed contacts the para-xylene selective adsorbent (not shown) under the aforementioned conditions, and para-xylene and ethylbenzene present in the feed are adsorbed by the adsorbent, while other components of the feed are not adsorbed and, thus, are eventually displaced (by incoming feed) from a top portion 52 of the first bed 42 via an outlet line 54 as a para-xylene depleted raffinate. The raffinate can be heated, if necessary, and passed directly to a downstream isomerization unit to obtain an equilibrated mixture of xylene isomers combinable with the $C_8$ aromatics feed.

While the first bed 42 is adsorbing (A1), the second bed 44 is desorbing in the D1 desorption stage. Sweep gas is fed via an inlet line 56 to a top portion 58 of the second bed 44, effectively sweeping out through a bottom portion 60 of the second bed 44 an effluent containing the sweep gas, unadsorbed hydrocarbons, and other gas present in void spaces of the adsorbent and the second bed 42. The effluent from the D1 desorption stage exits the second bed 44 via an outlet line 62, the effluent containing the sweep gas and hydrocarbons with a composition similar to that of the feed.

While the first bed 42 is adsorbing (A1) and the second bed 44 is desorbing (D1), the third bed 46 is desorbing in the D2 desorption stage. As in the D1 desorption stage, during the successive D2 desorption stage, sweep gas is continuously fed via an inlet line 64 to a top portion 66 of the third bed 46, effectively sweeping out through a bottom portion 68 of the third bed 46 any hydrocarbons and other gas present in void spaces of the adsorbent and third bed 46 and adhering to the adsorbent. The desorption effluent from the D2 desorption stage exits the third bed 46 via an outlet line 70. Unlike the hydrocarbons in the effluent obtained from the D1 desorption stage, however, the hydrocarbons present in the effluent obtained from the D2 desorption stage are rich in para-xylene and ethylbenzene—substantially higher purity than that of the feed.

In a second part of the same cycle immediately following the first part, a $C_8$ aromatics feed is introduced to the bottom portion 68 of the third bed 46 over an identically long time period (A1) for adsorption therein, during which the first bed 42 undergoes the D1 desorption stage and the second bed 44 undergoes the D2 desorption stage in the manner described above. In a third and final part of the cycle immediately following the second part, a $C_8$ aromatics feed is introduced to the bottom portion 60 of the second bed 44 over an identically long time period (A1) for adsorption therein, during which the third bed 46 undergoes the D1 desorption stage and the first bed 42 undergoes the D2 desorption stage in the manner described above, thus completing the cycle relative to the first bed 42. In a continuous process, of course, the foregoing cycle is repeated.

The flow rate of sweep gas during the D2 desorption stage may be the same as or different compared to that of the D1 desorption stage. Depending upon the flow rate of the sweep gas, the effluent from the D2 desorption stage can contain a significant amount of sweep gas. Thus, to separate the sweep gas from the para-xylene and ethylbenzene, a condensation system of heat exchangers (condensers) 72 and recovery drum(s) 74 can be used to condense the para-xylene and ethylbenzene into a liquid, and separate the liquid from the sweep gas. Suitable condensation systems and optimization of such systems are known by those skilled in the art. The effluents from the condensation system are a liquid para-xylene and ethylbenzene product stream 76 and the separated non-condensable gas having substantially reduced hydrocarbon content 78. The D2 desorption effluent can be passed to suitable downstream processes to further process or purify the product into its constituent parts, namely para-xylene and ethylbenzene. While the hydrocarbon content of this separated gas is low, the purity of the para-xylene and ethylbenzene remaining therein is high. Thus, a portion of the separated gas 80 can be recycled to the feed 50 for the adsorption stage (A1). Recycling the separated gas permits additional recovery of the para-xylene and ethylbenzene from the feed, and it also provides a means to regulate the partial pressure of the hydrocarbons during the adsorption stage (A1). Alternatively or additionally, a portion of the separated gas 82 can be recycled and combined with fresh sweep gas fed to the beds. The amount of the separated gas recycled to each of the fresh feed and fresh sweep can be varied between 0 and 100%.

Figure 3:
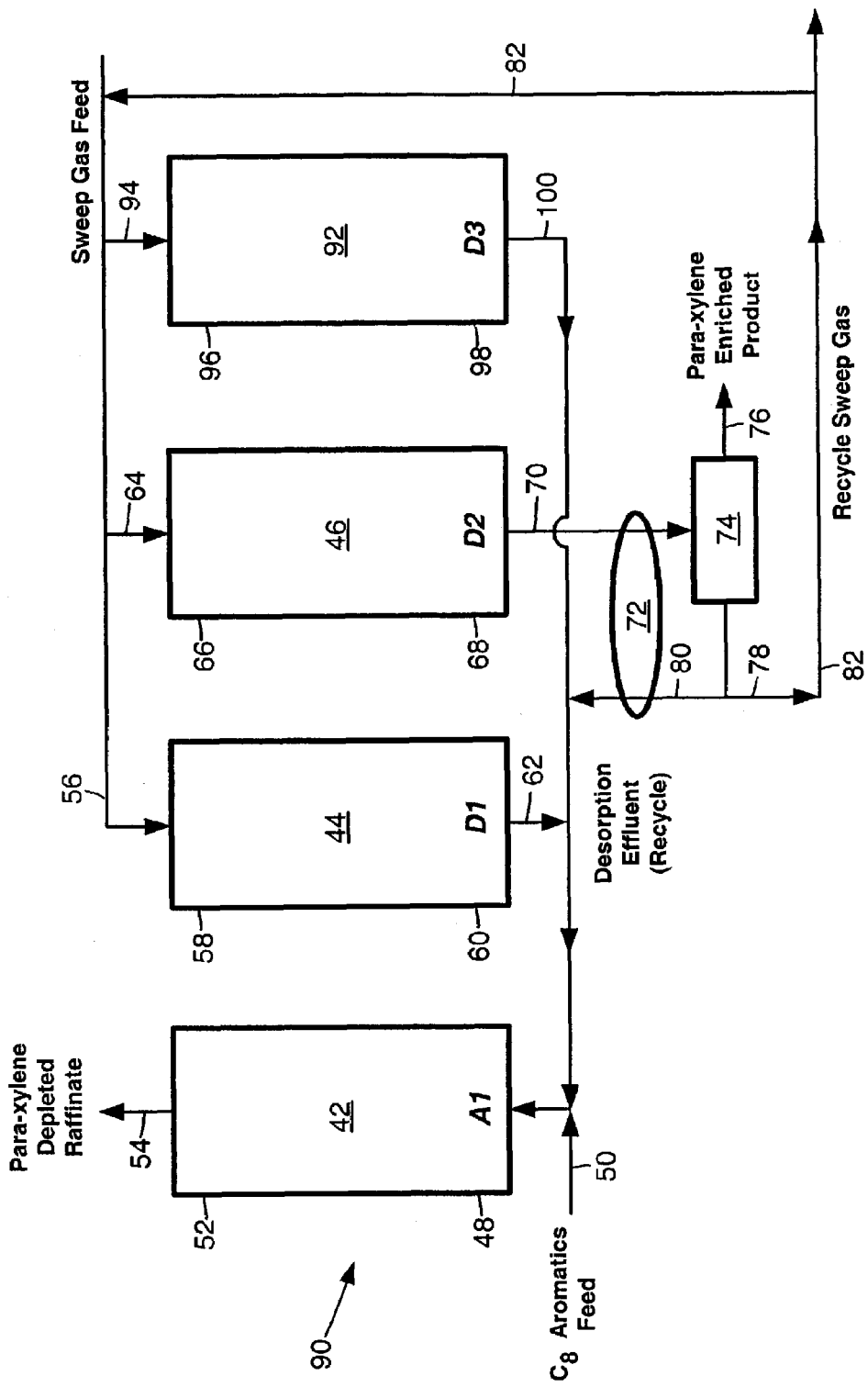
FIG. 3 is a process flow diagram illustrating one cycle of a four-bed PPSA suitable for carrying out the disclosed method.

Shown in FIG. 3 is a four-bed PPSA system 90 suitable for carrying out the disclosed method and, specifically, the contacting step therein. The four-bed PPSA system 90 includes many of the features of the three-bed PPSA system 40 described above and shown in FIG. 2. Notably different from the three-bed PPSA system 40, however, is the presence and operation of a fourth bed 92 in the four-bed PPSA system 90, and a third desorption stage (D3). In processes having only two desorption stages, the effluent from the second desorption stage will typically contain the desired product and during the stage there will be a point at which the effluent contains a maximum amount of the product. A benefit of the D3 desorption stage is that it provides an opportunity to end the D2 desorption stage just after the point of maximum product is attained, and to collect the remaining, less-pure product in the subsequent D3 stage.

As shown in FIG. 3, the system 90 includes four identical separation beds 42, 44, 46, and 92—"identical" in that each includes an adsorbent (not shown) and identical inlets and outlets, even though only certain inlets and outlets of each are shown and expressly described herein for purposes of more clearly illustrating a single cycle. Additional reference can be made to the following Table III:

TABLE III

| | Bed | | | |
|---|---|---|---|---|
| | First (42) | Second (44) | Third (46) | Fourth (92) |
| Stage | A1 | D1 | D2 | D3 |
| Stage | D1 | D2 | D3 | A1 |
| Stage | D2 | D3 | A1 | D1 |
| Stage | D3 | A1 | D1 | D2 |

As indicated in Table III and in FIG. 3, when the first bed 42 is adsorbing (A1), the second, third, and fourth beds 44, 46, and 92, respectively, are operating in desorption stages D1 through D3, respectively. Similarly, when the fourth bed 92 is adsorbing (A1), the first, second, and third beds 42, 44, and 46, respectively, are operating in desorption stages D1 through D3, respectively. When the third bed 46 is adsorbing (A1), the fourth, first, and second beds 92, 42, and 44, respectively, are operating in desorption stages D1 through D3, respectively. Finally, when the second bed 44 is adsorbing (A1), the third, fourth, and first beds 46, 92, and 42, respectively, are operating in desorption stages D1 through D3, respectively.

With the first bed 42 serving as a point of reference for the beginning of an on-going, four-part cycle, the first three beds operate in substantially the same manner as in the three-part cycle discussed above and shown in FIG. 2. While the first bed 42 is adsorbing (A1) and the second and third beds 44 and 46, respectively, are desorbing in desorption stages D1 and D2, respectively, the fourth bed 92 is desorbing in a third desorption stage, D3. As in the D1 and D2 desorption stages, during the successive D3 desorption stage, sweep gas is continuously fed via an inlet line 94 to a top portion 96 of the fourth bed 92, effectively sweeping out through a bottom portion 98 of the fourth bed 92 any hydrocarbons and other gas present in void spaces of the adsorbent and fourth bed 92. The desorption effluent from the D3 desorption stage exits the fourth bed 92 via an outlet line 100. Hydrocarbons present in the effluent obtained from the D3 desorption stage, though at a low partial pressure, are more rich in para-xylene than the feed, but not as rich as the effluent obtained from the D2 desorption stage. The D3 desorption effluent is similar to the gas exiting the recovery drum(s) 74 in that the effluent contains a small fraction of xylenes having a greater-than-equilibrium content of para-xylene. Because of this purity, the D3 desorption effluent can be advantageously recycled and combined with the feed to further improve the purity and yield of para-xylene in the D2 desorption effluent. An additional and non-obvious advantage of utilizing a four-bed PPSA system and the D3 desorption stage is that the sweep gas flow rate can be adjusted to accommodate a desired hydrogen to hydrocarbon ratio of the feed in the adsorption stage (A1) and, ultimately, of the raffinate being sent to the downstream isomerization unit.

Figure 4:
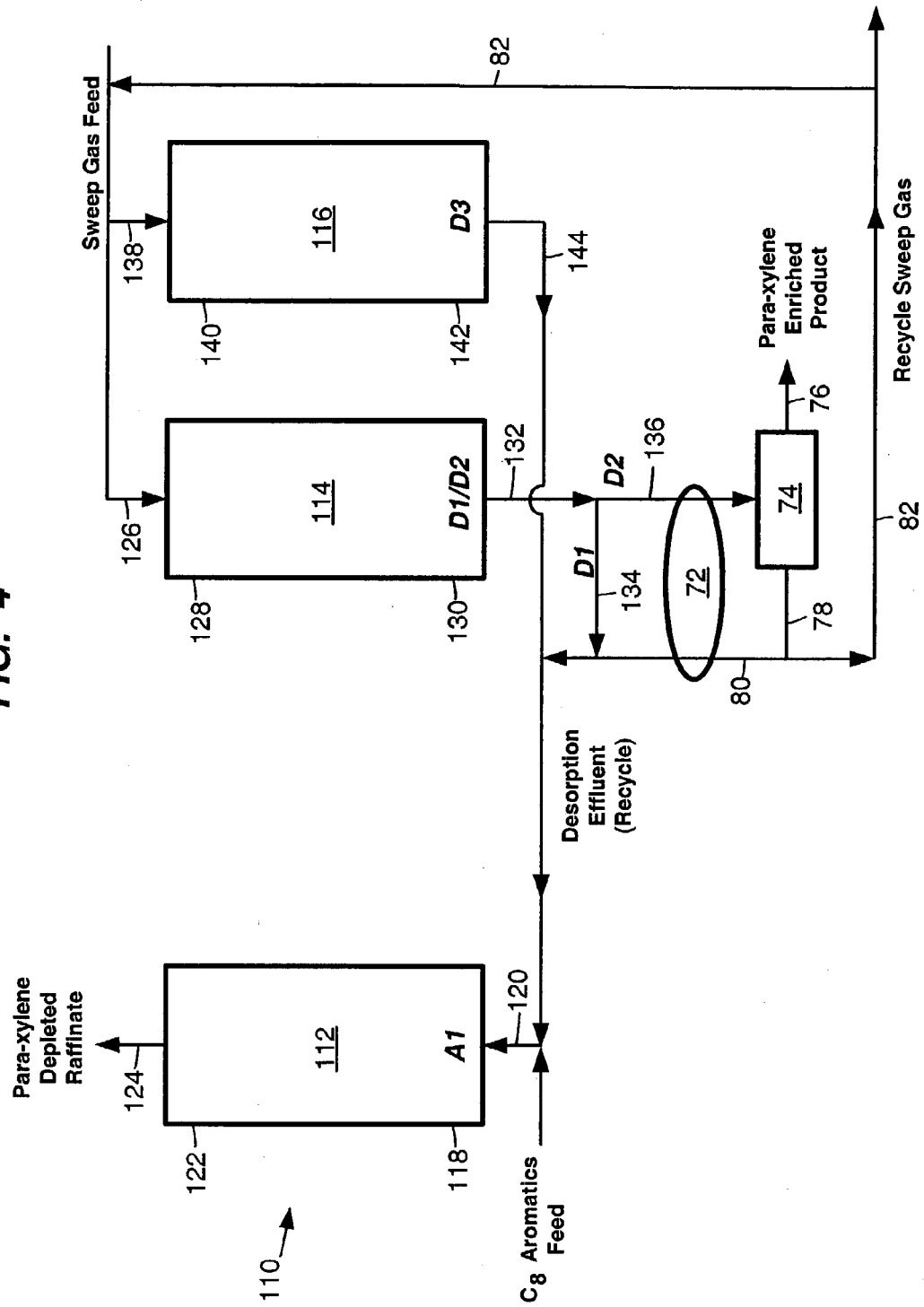
FIG. 4 is a process flow diagram illustrating one cycle of another three-bed PPSA system suitable for carrying out the disclosed method.

Shown in FIG. 4 is another three-bed PPSA system 110 suitable for carrying out the disclosed method and, specifically, the contacting step therein. As shown, the system 110 includes three identical separation beds 112, 114, and 116—"identical" in that each includes an adsorbent (not shown) and identical inlets and outlets, even though only certain inlets and outlets of each are shown and expressly described herein for purposes of more clearly illustrating a single cycle. Additional reference can be made to the following Table IV:

TABLE IV

| | Bed | | |
|---|---|---|---|
| | First (112) | Second (114) | Third (116) |
| Stage | A1 | D1 | D3 |
| Stage | A1 | D2 | D3 |
| Stage | D1 | D3 | A1 |
| Stage | D2 | D3 | A1 |
| Stage | D3 | A1 | D1 |
| Stage | D3 | A1 | D2 |

As indicated in Table IV and in FIG. 4, when the first bed 112 is adsorbing (A1), the third bed 116 is operating in the D3 desorption stage, and the second bed 114 is operating in one of desorption stages D1 and D2. Similarly, when the third bed 116 is adsorbing (A1), the second bed 114 is operating in the D3 desorption stage, and the first bed 112 is operating in one of desorption stages D1 and D2. Finally, when the second bed 114 is adsorbing (A1), the first bed 112 is operating in the D3 desorption stage, and the third bed 116 is operating in one of desorption stages D1 and D2.

With the first bed 112 serving as a point of reference for the beginning of an on-going, three-part cycle, in the first part, a $C_8$ aromatics feed is introduced to a lower portion 118 of the first bed 112 through an inlet line 120 over a time period (A1) during which the second bed 114 successively undergoes desorption stages D1 and D2, and the third bed 116 undergoes the D3 desorption stage. Within the first bed 112, the $C_8$ aromatics feed contacts the para-xylene selective adsorbent under the aforementioned conditions, and para-xylene and ethylbenzene present in the feed are adsorbed by the adsorbent, while other components of the feed are not adsorbed and, thus, are eventually displaced (by incoming feed) from a top portion 122 of the first bed 112 via an outlet line 124 as a para-xylene depleted raffinate. The raffinate can be heated, if necessary, and passed directly to a downstream isomerization unit to obtain an equilibrated mixture of xylene isomers combinable with the $C_8$ aromatics feed.

As shown, while the first bed 112 is adsorbing (A1), the second bed 114 undergoes desorption in successive desorption stages D1 and D2. Specifically, during desorption stage D1, sweep gas is fed via an inlet line 126 to a top portion 128 of the second bed 114, effectively sweeping out through a bottom portion 130 of the second bed 114 an effluent containing the sweep gas, unadsorbed hydrocarbons, and other gas present in void spaces of the adsorbent and second bed 114. The effluent from the D1 desorption stage exits the second bed 114 via an outlet line 132, the effluent containing the sweep gas and hydrocarbons with a composition similar to that of the feed mixture (or slightly enriched in para-xylene and ethylbenzene). The D1 desorption effluent in outlet line 132 is combined via line 134 with fresh feed mixture fed to the beds and any effluent from the desorption stage D3 (described hereinafter) to form a converged feed mixture for the adsorption stage (A1).

As in the D1 desorption stage, during the successive D2 desorption stage, sweep gas is continuously fed via the inlet line 126 to the top portion 128 of the second bed 114, effectively sweeping out through the bottom portion 130 of the second bed 114 any hydrocarbons and other gas present in void spaces of the adsorbent and second bed 114 and adhering to the adsorbent. The desorption effluent from the D2 desorption stage exits the second bed 114 via the outlet line 132. Unlike the hydrocarbons in the effluent obtained from the D1 desorption stage, however, the hydrocarbons present in the effluent obtained from the D2 desorption stage are rich in para-xylene and ethylbenzene—substantially higher purity than that of the feed.

The flow rate of sweep gas during the D2 desorption stage may be the same as or different compared to that of the D1 desorption stage. Depending upon the flow rate of the sweep gas, the effluent from the D2 desorption stage can contain a significant amount of sweep gas. Thus, to separate the sweep gas from the para-xylene and ethylbenzene in the D2 desorption effluent, the effluent is conveyed to a downstream condensation system of heat exchangers (condensers) 72 via a line 136 and subsequently to recovery drum(s) 74, which can be used to condense the para-xylene and ethylbenzene into a liquid, and separate the liquid from the sweep gas. As previously noted herein, suitable condensation systems and optimization of such systems are known by those skilled in the art. The effluents from the condensation system are a liquid para-xylene and ethylbenzene product stream 76 and the separated non-condensable gas having substantially reduced hydrocarbon content 78. The D2 desorption effluent can be passed to suitable downstream processes to further process or purify the product into its constituent parts, namely para-xylene and ethylbenzene. While the hydrocarbon content of this separated gas is low, the purity of the para-xylene and ethylbenzene remaining therein is high. Thus, a portion of the separated gas 80 can be recycled to the feed 120 for the adsorption stage (A1). Recycling the separated gas permits additional recovery of the para-xylene and ethylbenzene from the feed, and it also provides a means to regulate the partial pressure of the hydrocarbons during the adsorption stage (A1). Alternatively or additionally, a portion of the separated gas 82 can be recycled and combined with fresh sweep gas fed to the beds. The amount of the separated gas recycled to each of the fresh feed and fresh sweep can be varied between 0% and 100%.

While the first bed 112 is adsorbing (A1) and the second bed 114 undergoes desorption in successive desorption stages D1 and D2, the third bed is desorbing in desorption stage D3. As in the D1 and D2 desorption stages, during the successive D3 desorption stage, sweep gas is continuously fed via an inlet line 138 to a top portion 140 of the third bed 116, effectively sweeping out through a bottom portion 142 of the third bed 116 any hydrocarbons and other gas present in void spaces of the adsorbent and third bed 116. The desorption effluent from the D3 desorption stage exits the third bed 116 via an outlet line 144. Hydrocarbons present in the effluent obtained from the D3 desorption stage, though at a low partial pressure, are more rich in para-xylene than the feed, but not as rich as the effluent obtained from the D2 desorption stage. The D3 desorption effluent is similar to the gas exiting the recovery drum(s) 74 in that the effluent contains a small fraction of xylenes having a higher than equilibrium content of para-xylene. Because of this purity, the D3 desorption effluent can be advantageously recycled and combined with the feed to further improve the purity and yield of para-xylene in the D2 desorption effluent. An additional and non-obvious advantage of utilizing a four-bed PPSA system and the D3 desorption stage is that the sweep gas (e.g., hydrogen) flow rate can be adjusted to accommodate a desired gas-to-hydrocarbon ratio of the feed in the adsorption stage (A1) and, ultimately, of the raffinate being sent to the downstream isomerization unit.

In a second part of the same cycle immediately following the first part, a $C_8$ aromatics feed is introduced to the bottom portion 142 of the third bed 116 over an identically long time period (A1) for adsorption therein, during which the first bed 112 successively undergoes the D1 and D2 desorption stages and the second bed 114 undergoes the D3 desorption stage in the manner described above. In a third and final part of the cycle immediately following the second part, a $C_8$ aromatics feed is introduced to the bottom portion 130 of the second bed 114 over an identically long time period (A1) for adsorption therein, during which the third bed 116 successively undergoes the D1 and D2 desorption stages and the first bed 112 undergoes the D3 desorption stages in the manner described above, thus completing the cycle relative to the first bed 112. In a continuous process, of course, the foregoing cycle is repeated.

Reference in the foregoing discussion to "top" and "bottom" portions of adsorber beds is not intended to be limiting. As used herein, the terms "top" and "bottom" can be considered as opposing ends of the same bed. With appropriate piping, valves, and other process control equipment, certain of the inlets and outlets can be combined since, depending upon, whether the bed is in an adsorption or desorption stage, the inlets and outlets can convey different material. For example, and referring back to FIG. 1, the desorption effluent outlets 30 and 32 can be combined into one outlet with a valve therein capable of controlling where in the downstream process the effluent is to be sent (e.g., recycle or reject in the case of the D1 desorption effluent, or to para-xylene product refining in the case of the D2 desorption effluent). Similarly, the outlet 22 (in the first bed 12) for the para-xylene depleted raffinate can serve as an inlet for sweep gas during the desorption stages, and the inlet 24 (in the second bed 14) for the sweep gas can serve as the outlet for the para-xylene depleted raffinate during the adsorption stage.

Figure 5:
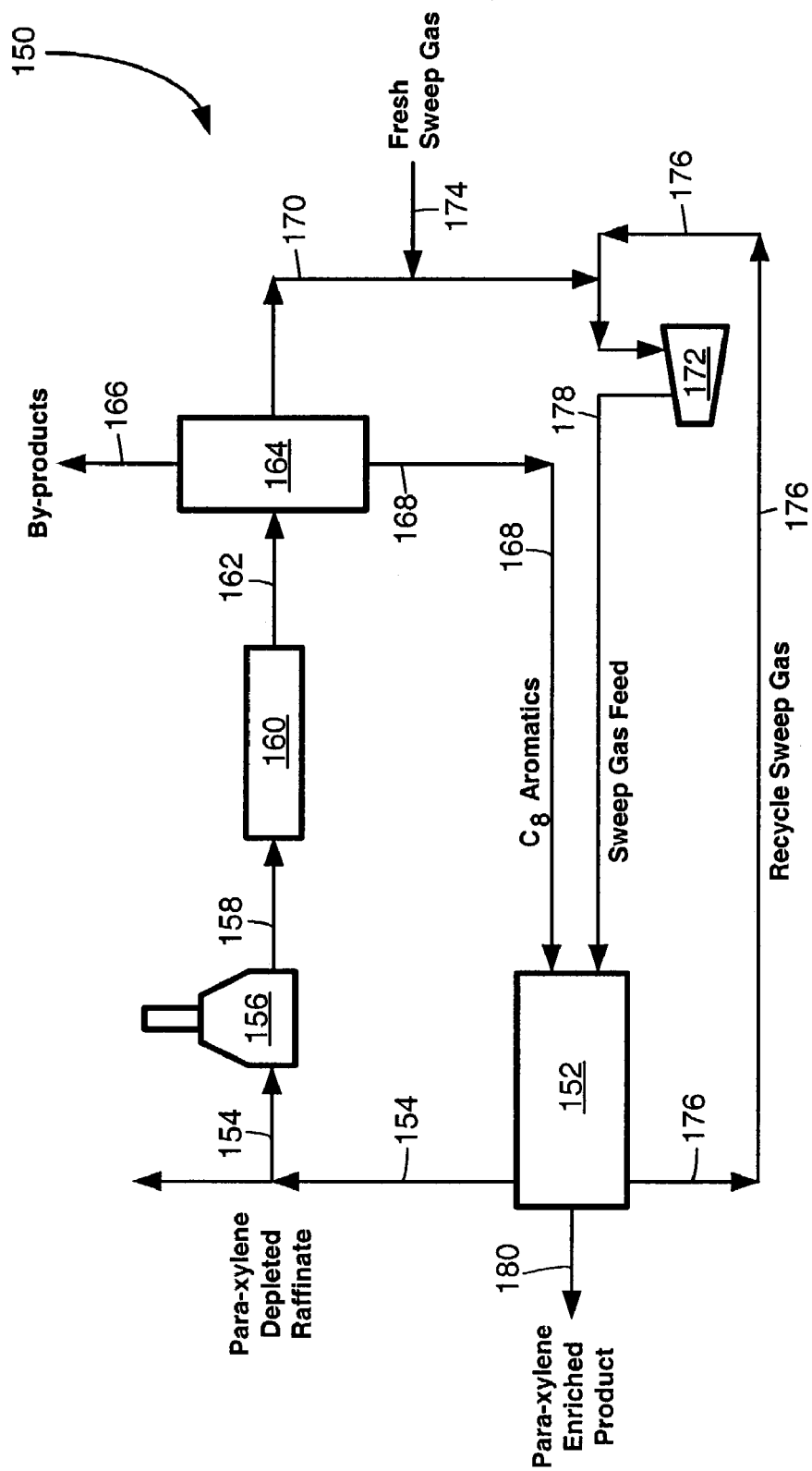
FIG. 5 is a process flow diagram illustrating an example of a process integrating the PPSA systems shown in FIGS. 1 through 4, and described herein.

Shown in FIG. 5 is a process flow diagram illustrating an example of a process 150 integrating the aforementioned PPSA systems. The process includes one of the aforementioned PPSA systems (shown in FIGS. 1 through 4) or appropriately modified systems thereof, designated 152 in FIG. 5. Exiting the PPSA system 152 via a line 154 is a para-xylene depleted raffinate, which is passed to a heater/furnace 156 to increase the temperature of the raffinate (if necessary) to a temperature suitable for downstream isomerization. Exiting the heater/furnace 156 via a line 158 is the heated raffinate, which is next passed to an isomerization unit 160 to obtain an equilibrated mixture of xylene isomers. Exiting the isomerization unit 160 via a line 162 is an isomerized product mixture containing the aforementioned mixture of xylene isomers as well as other by-products. The isomerized product mixture in line 162 is passed to a separation unit 164, wherein the by-products are separated and exit the process 150 via a line 166, $C_8$ aromatics are separated and exit the separation unit 164 via a line 168, and inert (sweep) gas present in the isomerized product mixture is separated and passed via a line 170 to a downstream compressor 172. Fresh sweep gas can enter the process via a line 174. Additionally, sweep gas from the PPSA system 152 can be collected and recycled via a line 176 to the other sweep gas streams 170 and 174, which then can be passed into the downstream compressor 172. Once compressed, the sweep gas exits the compressor 172 and is passed into the PPSA system 152 via a line 178. Exiting the PPSA system, of course, is a desired product stream in line 180 containing para-xylene and ethylbenzene. This desired product stream can be passed to other suitable downstream processes (not shown) to further process or purify the product into its constituent parts, namely para-xylene and ethylbenzene. Additionally, a portion of the para-xylene depleted raffinate can be passed to other suitable downstream processes (not shown) to further process or purify the raffinate to its primary constituent parts, namely meta-xylene, ortho-xylene, and sweep gas.

As noted above, subsumed in the disclosed method (and the various embodiments thereof) is an understanding by those skilled in the art of suitable processing equipment and controls necessary to carry out the method. Such processing equipment includes, but is not limited to, appropriate piping, pumps, valves, unit operations equipment (e.g., reactor vessels with appropriate inlets and outlets, heat exchangers, separation units, etc.), associated process control equipment, and quality control equipment, if any. For example, a plurality of separation steps and complex equipment can be used as needed to resolve the isomerized product mixture in the separation unit 164. Importantly, however, the disclosed method is advantageous over other methods in that no compression equipment is necessary between the PPSA system 152 and the downstream isomerization unit 160 and, therefore, none is shown in FIG. 5.

A fresh feed of xylene isomers to the PPSA system 152 and any downstream recycle streams (e.g., from the downstream para-xylene/ethylbenzene purification unit) are not shown in FIG. 5. Such fresh feed and recycle can be integrated in the process shown in FIG. 5 in a variety of locations to accomplish different goals. For example, these streams can be introduced directly into the PPSA system 152. Alternatively, or additionally, portions of these streams also can be introduced into the separation unit 164 to help minimize further processing of byproducts. Alternatively, or additionally, portions of these streams can be introduced into the furnace/heater 156 (if used) or the isomerization unit 160 to somewhat dilute the ethylbenzene, and any non-$C_8$ aromatics sent to be reduced in the isomerization unit 160 and separated in separation unit 164. Any of these options can be considered as part of the present invention.

Given the foregoing disclosure, these and other equipment modifications should be within the purview of those skilled in the art.

EXAMPLES

The following examples are provided to illustrate the method, but are not intended to limit the scope thereof.

Example 1 is directed to the preparation of a para-xylene selective adsorbent that was subsequently used to carry out the disclosed method in the manner set forth in the subsequent examples. Example 2 is directed to a partial pressure swing adsorption ("PPSA") sweep experiment carried out under various conditions in four separate runs in a two-bed PPSA system. Example 3 is directed to another PPSA sweep experiment carried out under various conditions in eleven separate runs in a two-bed PPSA system. Example 4 is directed to process modeling and attendant considerations.

Example 1

As noted above, this example is directed to the preparation of the para-xylene selective adsorbent that was subsequently used to carry out the disclosed method in the manner set forth in the subsequent examples.

A para-xylene selective adsorbent was prepared by formulation of 80 wt. % silicalite and 20 wt. % binder (85 wt. % calcium clay and 15 wt. % silica, based on the total weight of the binder), based on the total weight of the adsorbent. The silicalite has the MFI structure type and can be prepared from a variety of standard procedures. A typical procedure is to combine 18.4 grams sodium hydroxide (NaOH) and 12.8 grams tetrapropylammonium bromide in 227.6 grams of water. After dissolution, 122.6 grams Nalco 2327 silica sol (40 wt. % silica) was added and stirred for two hours. Concentrated sulfuric acid ($H_2SO_4$) was slowly added to achieve a pH of 13. The resulting solution was heated under autogenous pressure in a TEFLON™-lined autoclave for one to seven days at 300° F. (149° C.).

Example 2

As noted above, this example is directed to a partial pressure swing adsorption ("PPSA") sweep experiment carried out in a two-bed PPSA system according to the conditions in the upper portion of Table V (below). The adsorbent prepared in Example 1 was used in the separation beds for the various Runs described below. Results from the Runs are shown in the lower portion of Table V. The yield and recovery of component X and the recycle yield are defined according to the following equations:

$$\text{Yield of } X\,(\%) = \frac{\text{Weight of } X \text{ Collected in Stream}}{\text{Weight of } X \text{ in Feed}} \times 100$$

$$\text{Recovery of } X\,(\%) = \frac{\text{Weight of } X \text{ Collected in Stream}}{(\text{Weight of } X \text{ in Feed}) - (\text{Weight of } X \text{ in Recycle})} \times 100$$

$$\text{Recycle Yield}\,(\%) = \frac{\text{Weight of Recycle Collected}}{\text{Weight of Feed}} \times 100$$

TABLE V

|  | Run | | | |
|---|---|---|---|---|
|  | A | B | C | D |
| Temperature (° C.) | 251 | 251 | 249 | 276 |
| Pressure (kPa) | 414 | 807 | 690 | 1890 |
| Sweep Flow (SCFH† $N_2$) | 15.4 | 30.0 | 15.4 | 50.0 |
| Feed HC Flow (g/min) | 20.1 | 19.6 | 23.7 | 21.2 |
| Feed $N_2$/HC Flow (mol/mol) | 0.0 | 1.1 | 0.0 | 1.8 |
| Wt. % pX + EB in HC Feed | 27.4 | 27.4 | 27.4 | 32.4 |
| Wt. % mX + oX in HC Feed | 72.6 | 72.6 | 72.6 | 67.6 |
| A1 Stage Time (seconds) | 64 | 64 | 64 | 64 |
| D1 Stage Time (seconds) | 18 | 12 | 12 | 17 |
| D2 Stage Time (seconds) | 46 | 52 | 52 | 47 |
| D2 pX + EB Recovery (%) | 85.0 | 84.0 | 85.0 | 88.2 |
| D2 pX + EB Purity (wt. %) | 82.3 | 80.7 | 73.1 | 83.6 |
| A1 mX + oX Purity (wt. %) | 96.3 | 94.1 | 94.8 | 94.9 |
| D1 Recycled Yield (%) | 25.0 | 20.0 | 25.0 | 31.0 |
| D1 Recycle pX + EB Purity (wt. %) | 37.7 | 31.5 | 28.4 | 40.2 |

†SCFH is an abbreviation for standard cubic feet per hour.

Two separation units (beds) were arranged in series and contained the adsorbent described in Example 1. Four separate runs were conducted according to the conditions reported in Table V (i.e., temperature, pressure, nitrogen gas sweep flow rate, $C_8$ feed ("HC") mass flow rate, molar flow of inert (nitrogen) gas per mole of HC, and the composition of the HC feed), wherein the four runs are identified as runs A through D. Slight variations in the reported conditions are readily apparent from a review of Table V and the impact(s) on the process are set forth hereinafter.

The two-bed PPSA system used in this example is the one shown in FIG. 1, and further described in Table I and the accompanying descriptions of the same. More specifically, and with reference to Run "A," a $C_8$ feed was introduced to the first bed over a time period of 64 seconds (A1), during which period the second bed underwent two different desorption stages, the first of which lasted a time period of 18 seconds (D1), and the second of which lasted 46 seconds (D2). Immediately thereafter, a $C_8$ feed was introduced to the second bed over another 64 second time period (A1), during which period the first bed underwent two different desorption stages, the first of which lasted 18 seconds (D1), and the second of which lasted 46 seconds (D2).

Desorption was carried out with the aid of an inert sweep gas (nitrogen). The entirety of the desorption effluent obtained via the first desorption stage D1 was collected as a recycle product in each of Runs A through C, but was not actually recycled; however, it was recycled in Run D. Normally, in a continuous process, portions of the effluent from the first desorption stage D1 would be combined with the feed to further increase purity and recovery of the overall process. The raffinate contained predominantly meta-xylene and ortho-xylene. The D1 desorption effluent contained predominantly excess feed, unadsorbed hydrocarbons, and nitrogen. The D2 desorption effluent contained predominantly para-xylene, ethylbenzene, and nitrogen. In practice, a portion of the D2 desorption effluent can be refined to remove the nitrogen and then recycled (though it was not in any of Runs A through D of this example).

Multiple runs were conducted under the various different conditions to determine the recovery and purity levels achievable, keeping in mind downstream unit operations necessary to isomerize, for example, the raffinate containing predominantly meta- and ortho-xylenes. As previously noted herein, commercial xylene isomerization reactors typically operate at a pressure within a range of about atmospheric pressure to about 6895 kPa (about 1000 psia), and more typically at a pressure within a range of about 345 kPa to about 2757 kPa (about 50 psia to about 400 psia), and at a temperature with a range of about 200° C. to about 550° C.

While the results from Run A appeared promising, integration of the para-xylene depleted raffinate with an isomerization reactor would have necessitated multiple heat exchangers and pumps, as well as a significantly increased furnace capacity to adequately raise the raffinate's temperature and pressure prior to feeding it to the isomerization reactor. Given the conditions of the raffinate and the required xylene isomerization conditions, such equipment would be very expensive from both capital expenditure and continuous operations standpoints.

In Run B, a higher para-xylene depleted raffinate pressure was achieved by co-feeding an inert gas, specifically nitrogen, with the $C_8$ aromatics mixture to the beds during the adsorption stage. Compared to Run A, the-hydrocarbon partial pressure was maintained at a nearly constant level, but at a higher total pressure in the bed. The results from Run B are essentially identical to the results obtained in Run A with only small changes in the observed purities and recoveries. Advantageously, the para-xylene depleted raffinate stream in Run B exited the adsorption bed at a pressure of about 807 kPa (about 117 psia) and, therefore, would integrate directly into the desirable range of operating pressures for xylene isomerization reactors.

In Run C, the total pressure was increased by increasing only the hydrocarbon pressure (i.e., no inert gas was included with the $C_8$ aromatics mixture fed to the adsorption beds). The results from Run C show that the observed para-xylene and ethylbenzene (pX+EB) purity decreased from 82.3 wt. % (in Run A) to 73.1 wt. %. This decrease illustrates that the addition of an inert gas to the $C_8$ aromatics mixture fed to the adsorption unit provides desirably significant and unobvious benefits.

In Run D, an attempt was made to mimic the behavior of an operating PPSA sweep process with recycle. Because of the recycle and the attendant higher concentration of para-xylene and ethylbenzene therein, the composition of the $C_8$ aromatics fed to the adsorption unit had a higher concentration of para-xylene and ethylbenzene (32.4 wt. %) compared to the prior Runs A, B, and C (27.4 wt. %). Also, the amount of nitrogen co-feed was increased to reflect that the recycle also contained gas, which would be recycled along with the hydrocarbons. Computer simulation of a material balance of the converged process (i.e., one with recycle) was used to predict these changes. The results from Run D show that at even higher temperatures and pressures, high purity and recovery are obtainable in this type of process. Such a pressure is ideal for integration with a downstream isomerization reactor with only the need for temperature adjustment of the raffinate. Thus, expensive compressors between the adsorption unit and the isomerization unit are not needed.

Example 3

As noted above, this example is directed to a PPSA experiment carried out in a two-bed PPSA system utilizing the adsorbent prepared in Example 1. More specifically, in this example, eleven runs (labeled Runs E through N, below) were conducted wherein the duration of the desorption stages D1 and D2 was changed in each run to determine an optimal duration for each stage at which purity of para-xylene and ethylbenzene is maximized. The duration of the adsorption stage A1 was maintained at 128 seconds in each run. The D1 desorption stage time was varied between 50 seconds and 123 seconds, and the D2 desorption stage time was varied between 5 seconds and 78 seconds—thus, in any given run, the aggregated time for the two desorption stages remained constant at 128 seconds. For a more detailed description of the adsorption and desorption stages, reference should be made to FIG. 1, Table I, and the descriptions accompanying the same, as well as to Example 2.

Eleven separate runs were conducted according to the conditions reported in Table VI (i.e., temperature, pressure, nitrogen gas sweep flow rate, $C_8$ feed ("HC") mass flow rate, molar flow of inert (nitrogen) gas per mole of HC, and the composition of the HC feed), below.

TABLE VI

| Conditions | Runs E-N |
| --- | --- |
| Temperature (° C.) | 223 |
| Pressure (kPa) | 414 |
| Sweep Flow (SCFH $N_2$) | 9.25 |
| Feed HC Flow (g/min) | 7.0 |
| Feed $N_2$/HC Flow (mol/mol) | 0.0 |

TABLE VI-continued

| Conditions | Runs E-N |
|---|---|
| Wt. % pX + EB in HC Feed | 35.6 |
| Wt. % mX + oX in HC Feed | 64.4 |

Given the foregoing conditions for each of Runs E through N, the following recovery and yield data were obtained when the durations of the desorption stages D1 and D2 were varied. The data are set forth in Table VII, below.

TABLE VII

| Run | D1 Stage Time (sec) | D2 Stage Time (sec) | Total Feed (g) | pX + EB product (g) | D2 pX + EB Yield (%) | D2 pX + EB $P_o$ (wt %) | D2 pX + EB Recovery (%) |
|---|---|---|---|---|---|---|---|
| E | 50 | 78 | 454.4 | 62.5 | 38.6 | 69.7 | 96.3 |
| F | 50 | 78 | 454.4 | 62.5 | 38.6 | 69.3 | 96.3 |
| G | 88 | 40 | 442.0 | 42.6 | 27.1 | 69.9 | 94.8 |
| H | 100 | 28 | 448.4 | 35.5 | 22.2 | 63.0 | 93.7 |
| I | 118 | 10 | 448.0 | 27.1 | 17.0 | 62.5 | 91.9 |
| J | 118 | 10 | 448.0 | 28.5 | 17.9 | 62.6 | 92.3 |
| K | 118 | 10 | 441.6 | 26.9 | 17.1 | 62.2 | 91.9 |
| L | 123 | 5 | 441.6 | 5.0 | 3.2 | 47.7 | 68.0 |
| M | 123 | 5 | 473.6 | 4.4 | 2.6 | 46.0 | 63.3 |
| N | 123 | 5 | 428.8 | 3.8 | 2.5 | 47.0 | 62.4 |

Figure 6:
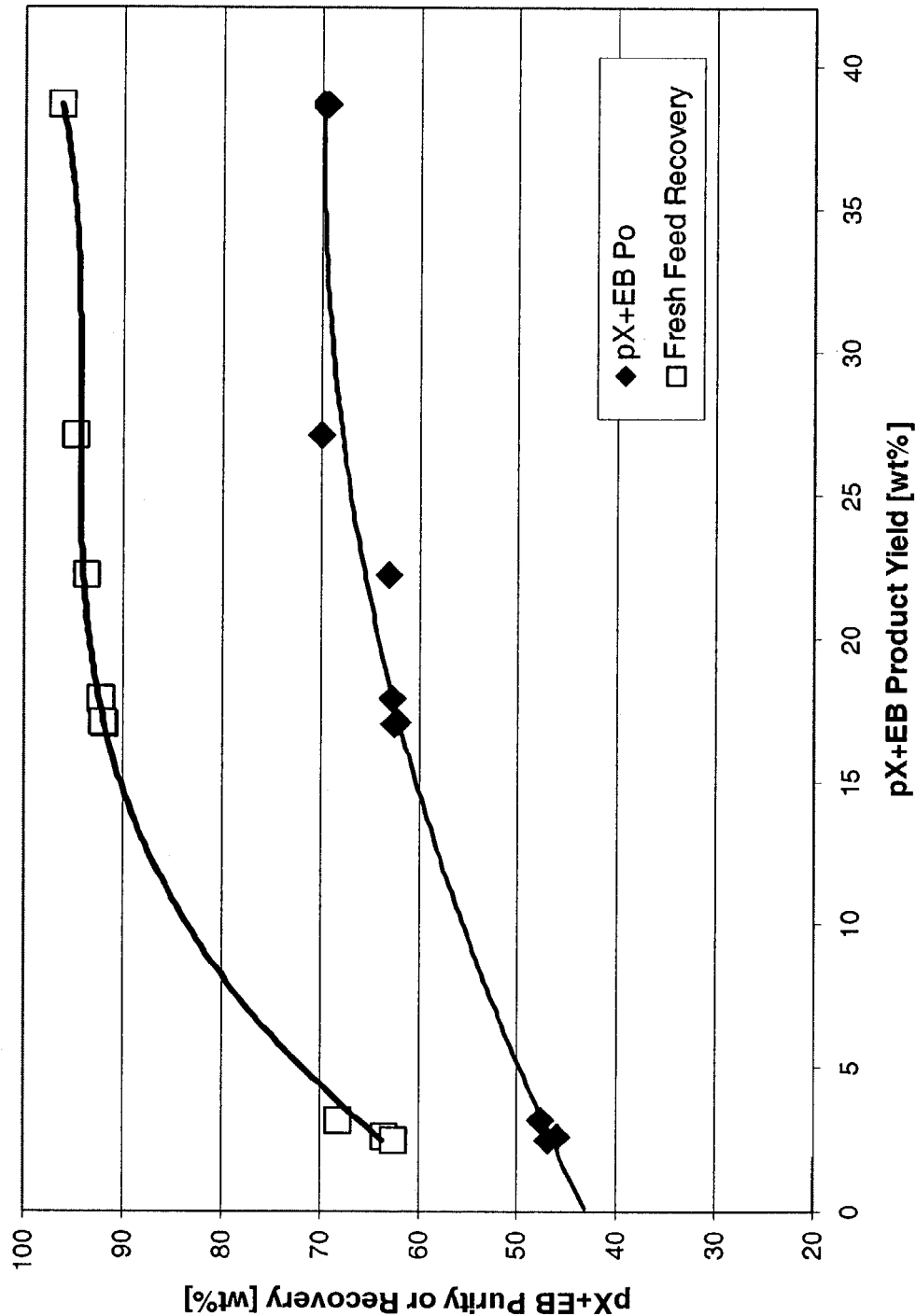
FIG. 6 is a graph plotting para-xylene and ethylbenzene yield versus recovery in connection with Example 3; and, FIG. 7 is a graph showing compositions of various streams of a simulated PPSA system in connection with Example 4.

The observed purity of para-xylene and ethylbenzene ($P_o$) was determined directly from an analysis of the accumulated product stream from D2. Instantaneous purity of para-xylene and ethylbenzene ($P_i$) is defined as the para-xylene and ethylbenzene purity of the hydrocarbon stream exiting the bed at a given moment in time. Direct measurement of the instantaneous purity ($P_i$) is a complicated analytical problem, but by varying the durations of the D1 and D2 desorption stages while maintaining a constant desorption time of 128 seconds, it is possible to observe the purity of different fractions of the total material collected in the recycle and product streams. Table VII, above, and FIG. 6 summarize the obtained data.

Based on the obtained data, Runs L through N show that the D1 and D2 desorption stage times of 123 seconds and 5 seconds, respectively, resulted in the lowest product yield. In those runs, the collected product corresponds to the last portion of hydrocarbon swept from the bed during the combination of the desorption stages D1 and D2. The purity of the product stream in these runs was about 47 wt. %. The product yield and observed purity ($P_o$) of the para-xylene and ethylbenzene increased as the D2 desorption stage time increased. For example, a D2 desorption stage time of 10 seconds yielded a product with an observed purity ($P_o$) of about 62 wt. %. For the observed purity ($P_o$) to increase in this manner, the instantaneous purity ($P_i$) of the earlier material (e.g., that material collected before in the preceding 123 seconds) must have had a higher instantaneous purity ($P_i$) than the material collected between the first 123 and 128 seconds. This observation continues to be true for shorter D1 desorption stages (and longer D2 desorption stages).

Without being bound by any particular theory, it is believed that this phenomena occurs because the separation of xylenes on medium pore zeolites is kinetic and based upon molecular size. Medium pore zeolites, such as MFI, typically have pore openings of about 5.4 angstroms (Å) to about 5.8 Å. Para-xylene and ethylbenzene molecules have kinetic diameters of about 5.9 Å and about 6.0 Å, respectively, and, therefore, will adsorb much more quickly than meta- and ortho-xylene molecules (which have kinetic diameters of about 6.8 Å). While the meta- and ortho-xylene molecules do adsorb to some extent, they do so at a rate much slower than that at which para-xylene and ethylbenzene adsorb. Conventional shape-selective, adsorptive processes, such as the ISOSIV™ processes (which are directed to separation of paraffins), teach that the other components do not adsorb to any significant extent. This is true for the case of iso-paraffins on small-pore zeolite A. Alternatively, equilibrium-based separations would suggest that the product purity continues to increase during the desorption stage rather that decrease as the above data illustrate (Ralph T. Yang, "Gas Separation by Adsorption Processes," pp. 237-274 (Butterworth Publishers, Boston, 1987) (TP242.Y36)).

The data show that collecting the last portion of the product in a sweep-based PSA process based on a kinetic separation generally lowers the observed product purity because that portion of the product, in fact, has a lower purity. This result is not obvious based on prior art or the observed purity ($P_o$) data collected during a conventional swing-adsorption experiment. Preferably, the practiced method is capable collecting the product at the point of maximum instantaneous purity ($P_i$), the determination of which can be made by routine optimization techniques known by those skilled in the art.

Example 4

The PPSA process can be modeled by computer simulation. The model used in this example is composed of a single bed of adsorbent material according to the conditions described in Example 2. As part of the simulation, the adsorbent bed is subdivided along its length into ten equal zones that are assumed to be well-mixed. Each zone contains solid adsorbent and void space that are modeled independently. The model adsorbent can adsorb both ethylbenzene and all of the xylene isomers, but the rates of adsorption and desorption depend upon the structure of the aromatic molecule. Para-xylene and ethylbenzene both adsorb quickly and, thus, are considered as a single component. Meta-xylene and ortho-xylene adsorb much more slowly and, thus, are considered as a separate single component. For each of these separate components, the mass-transfer rates between the void space and the adsorbent were fit to experimental data by use of adsorption isotherms and a linear, driving force approximation. As the simulation progressed, the flows into the top and bottom of the bed were alternated to simulate stages of the PPSA cycle.

Figure 7:
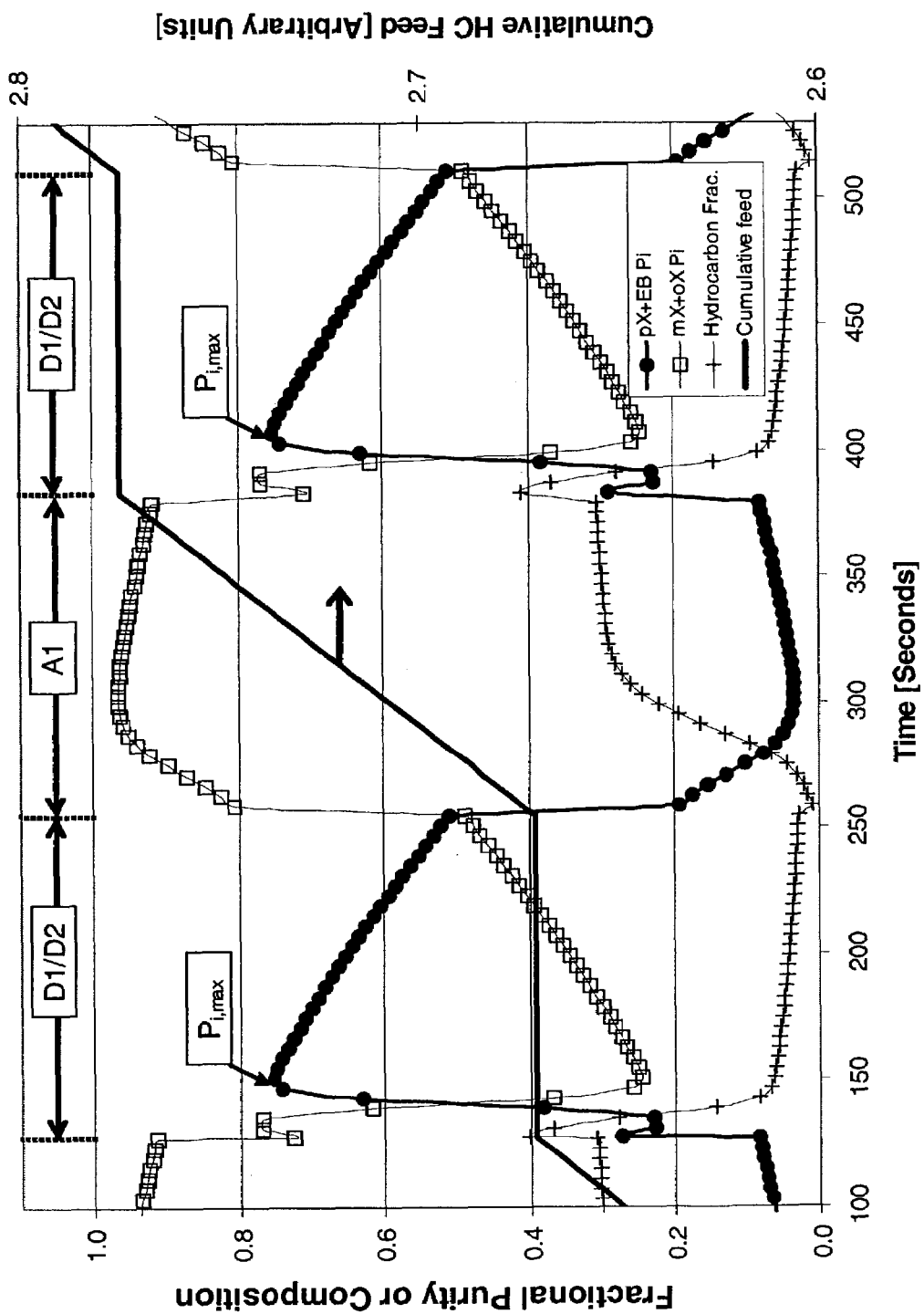

FIG. 7 shows the cumulative feed, effluent instantaneous purity (Pi), and effluent composition for one absorber bed operating under constant total pressure, cyclic partial pressure sweep operation. At about 128 seconds, the bed entered the desorption stages (e.g. D1, D2, etc). Feed was not admitted during this time as indicated by the constant cumulative feed curve. At about 150 seconds, the effluent reached a peak in para-xylene and ethylbenzene purity. After this time, the para-xylene and ethylbenzene purity decreased. The hydrocarbon content of the stream decreased rapidly as the desorption stages progressed. At about 254 seconds, the hydrocarbon feed was once again initiated for the adsorption stage (A1). At this point, the effluent stream became more rich in meta-xylene and ortho-xylene as the para-xylene and ethylbenzene were adsorbed. At about 382 seconds, the bed re-entered desorption as cyclic operation continued.

During the adsorption stage (A1), the composition exiting the top of the bed contained substantially reduced quantities of para-xylene and ethylbenzene compared to the feed, which in this example, had a para-xylene and ethylbenzene fraction of 0.278. However, when the hydrogen sweep gas was fed to the top of the bed, the para-xylene and ethylbenzene composition exiting the bottom of the bed increased and proceeded to a maximum purity (as indicated in FIG. 7) before the adsorption stage (A1) began.

Preferably, the product has the highest possible purity, and generally greater than about 65 wt. % para-xylene and ethylbenzene is most preferable. Specifying the sweep effluent between about 140 and 220 seconds (FIG. 7) as product for the present simulation would yield the most material at the highest possible purity. This would correspond to the D2 desorption stages of Examples 2 and 3, and in the two-, three-, and four-bed PPSA systems described above. The effluent obtained prior to about 140 seconds had a significantly lower purity and could have been recycled directly to the feed to increase overall para-xylene recovery. This would correspond to the D1 desorption stage described in Examples 2 and 3, and in the two-, three-, and four-bed PPSA systems described above. The effluent obtained after about 220 seconds still had a higher purity than the feed, but a low partial pressure of xylenes (low hydrocarbon fraction). This portion of the effluent could also have been recycled to the feed to both increase the overall para-xylene recovery and improve integration with the isomerization reactor. This would correspond to the D3 desorption stage as described above with respect to the three- and four-bed PPSA systems.

The raffinate containing predominantly meta-xylene and ortho-xylene exits the PPSA system with a hydrocarbon fraction of about 0.3, which corresponds to a hydrogen:hydrocarbon ($H_2$:HC) ratio of about 2.3. A ratio considered acceptable for a feed to the isomerization reactor is in a range of about 0.1 to about 10. Thus, the 2.3 ratio obtained herein falls within the acceptable range. The $H_2$:HC ratio of the meta-xylene and ortho-xylene product can be controlled by adjusting the sweep gas flowrate between time period of about 220 seconds and the beginning of the next adsorption stage (e.g. during the D3 desorption stage). Thus, the meta-xylene and ortho-xylene PPSA raffinate can be heated and directly fed into the isomerization reactor without subsequent processing steps (e.g., compression) and without addition or subtraction of any material. Under these circumstances, there was no need for additional compression equipment and, because the para-xylene and ethylbenzene recovery is high (about 87 wt. %), an increased yield was achievable in the isomerization reactor.

The foregoing description is given for clearness of understanding only, and no unnecessary limitations should be understood therefrom, as modifications within the scope of the invention may be apparent to those having ordinary skill in the art.

What is claimed is:

1. A method comprising the steps of:
   (a) contacting at a substantially non-decreasing total pressure (i) a gaseous mixture comprising xylene isomers, ethylbenzene, and a non-adsorbable gas, with (ii) a para-xylene selective adsorbent comprising a medium pore zeolite to obtain a para-xylene depleted raffinate and a desorption effluent comprising a para-xylene enriched product, wherein the non-adsorbable gas comprises hydrogen and is non-reactive with the xylene isomers and ethylbenzene during the contacting step; and,
   (b) isomerizing at least a portion of the para-xylene depleted raffinate.

2. The method of claim 1, wherein step (b) further comprises isomerizing the para-xylene depleted raffinate at a pressure that is equal to or less than the substantially non-decreasing total pressure.

3. The method of claim 2, wherein step (b) further comprises isomerizing the para-xylene depleted raffinate at a pressure that is less than the substantially non-decreasing total pressure.

4. The method of claim 1, wherein the sum of the partial pressures of the xylene isomers and ethylbenzene is less than the substantially non-decreasing total pressure.

5. The method of claim 4, wherein the sum is about 15% to about 99.5% of the substantially non-decreasing total pressure.

6. The method of claim 1, wherein the para-xylene depleted raffinate comprises hydrocarbons substantially free of para-xylene, and the gas is present in an amount sufficient to provide a gas-to-hydrocarbon mole ratio in the para-xylene depleted raffinate of about 0.1:1 to about 10:1.

7. The method of claim 1, wherein the gas is present in an amount sufficient to ensure that the substantially non-decreasing total pressure is equal to or greater than an isomerization step pressure, while maintaining the partial pressure of the xylene isomers and ethylbenzene at or below the respective condensation pressures of the xylene isomers and ethylbenzene.

8. The method of claim 7, wherein the gas is present in an amount sufficient to avoid condensation of the xylene isomers.

9. The method of claim 1, wherein the gas further comprises one or more materials selected from the group consisting of argon, carbon dioxide, helium, nitrogen, methane, ethane, propane, and butane.

10. The method of claim 1, wherein the para-xylene depleted raffinate comprises meta-xylene, ortho-xylene, and hydrogen.

11. The method of claim 1, wherein step (b) further comprises isomerizing the para-xylene depleted raffinate to obtain a hydrocarbon mixture comprising equilibrated xylene isomers.

12. The method of claim 11, further comprising combining at least a portion of the xylene isomers obtained in step (b) with the mixture in step (a).

13. The method of claim 1, further comprising separating substantially pure para-xylene from the desorption effluent.

14. The method of claim 13, further comprising separating substantially pure para-xylene from the desorption effluent at a pressure that is equal to or less than the substantially non-decreasing total pressure.

15. The method of claim 14, further comprising separating substantially pure para-xylene from the desorption effluent at a pressure that is less than the substantially non-decreasing total pressure.

16. A method comprising the steps or:
   (a) contacting at a first pressure (i) a mixture comprising xylene isomers, ethylbenzene, and a non-adsorbable gas, with (ii) a para-xylene selective adsorbent comprising a medium pore zeolite to obtain a para-xylene depleted raffinate and a desorption effluent comprising a para-xylene enriched product, wherein the non-adsorbable gas comprises hydrogen and is non-reactive with the xylene isomers and ethylbenzene during the contacting step; and,
   (b) isomerizing at a second pressure at least a portion of the para-xylene depleted raffinate, wherein the gas is present in an amount sufficient to ensure the first pressure is equal to or greater than the second pressure.

17. The method of claim 16, wherein the mixture in the contacting step (a) is a gaseous mixture.

18. The method of claim 16, wherein the first pressure is greater than the second pressure.

19. The method of claim 16, wherein the sum of the partial pressures of the xylene isomers and ethylbenzene is less than the first pressure.

20. The method of claim 19, wherein the sum is about 15% to about 99.5% of the first pressure.

21. The method of claim 16, wherein the para-xylene depleted raffinate comprises hydrocarbons substantially free of para-xylene, and the gas is present in an amount sufficient to provide a gas-to-hydrocarbon mole ratio in the para-xylene depleted raffinate of about 0.1:1 to about 10:1.

22. The method of claim 16, wherein the gas is present in an amount sufficient to maintain the partial pressure of the xylene isomers and ethylbenzene at or below the respective condensation pressures of the xylene isomers and ethylbenzene.

23. The method of claim 16, wherein the gas is present in an amount sufficient to avoid condensation of the xylene isomers.

24. The method of claim 16, wherein the gas further comprises one or more materials selected from the group consisting of argon, carbon dioxide, helium, nitrogen, methane, ethane, propane, and butane.

25. The method of claim 16, wherein the para-xylene depleted raffinate comprises meta-xylene, ortho-xylene, and hydrogen.

26. The method of claim 16, wherein step (b) further comprises isomerizing the para-xylene depleted raffinate to obtain a hydrocarbon mixture comprising equilibrated xylene isomers.

27. The method of claim 26, further comprising combining at least a portion of the xylene isomers obtained in step (b) with the mixture in step (a).

28. The method of claim 16, wherein the first pressure is a substantially non-decreasing pressure.

29. The method of claim 28, further comprising separating substantially pure para-xylene from the desorption effluent.

30. The method of claim 28, further comprising separating substantially pure para-xylene from the desorption effluent at a pressure that is equal to or less than the first pressure.

31. The method of claim 30, further comprising separating substantially pure para-xylene from the desorption effluent at a pressure that is less than the first pressure.

32. A method comprising the steps of:
(a) contacting a mixture comprising xylene isomers, ethylbenzene, and a non-adsorbable, non-reactive gas with a para-xylene selective adsorbent to obtain a para-xylene depleted raffinate and a desorption effluent comprising a para-xylene enriched product; and,
(b) isomerizing at least an unfractionated portion of the para-xylene depleted raffinate,
wherein the gas is present in an amount sufficient to ensure a raffinate pressure equal to or greater than an isomerization step pressure, while maintaining the partial pressure of the xylene isomers and ethylbenzene at or below the respective condensation pressures of the xylene isomers and ethylbenzene.

33. The method of claim 32, wherein the mixture in the contacting step (a) is a gaseous mixture.

34. The method of claim 32, wherein the gas is present in an amount sufficient to ensure a raffinate pressure greater than the isomerization step pressure.

35. The method of claim 32, wherein the gas is present in an amount sufficient to avoid condensation of the xylene isomers.

36. The method of claim 32, wherein the gas comprises one or more materials selected from the group consisting of hydrogen, nitrogen, and light paraffins.

37. The method of claim 36, wherein the gas comprises hydrogen.

38. The method of claim 37, wherein the para-xylene depleted raffinate comprises meta-xylene, ortho-xylene, and hydrogen.

39. The method of claim 32, wherein step (b) further comprises isomerizing the para-xylene depleted raffinate to obtain a hydrocarbon mixture comprising equilibrated xylene isomers.

40. The method of claim 39, further comprising combining at least a portion of the xylene isomers obtained in step (b) with the mixture in step (a).

41. The method of claim 32, wherein the contacting step (a) is carried out at a substantially non-decreasing total pressure.

42. The method of claim 41, further comprising separating substantially pure para-xylene from the desorption effluent.

43. The method of claim 42, further comprising separating substantially pure para-xylene from the desorption effluent at a pressure that is equal to or less than the substantially non-decreasing total pressure.

44. The method of claim 43, further comprising separating substantially pure para-xylene from the desorption effluent at a pressure that is less than the substantially non-decreasing total pressure.

45. A method comprising the steps of:
(a) contacting (i) a gaseous mixture comprising xylene isomers, ethylbenzene, and a non-adsorbable gas with (II) a para-xylene selective adsorbent comprising a medium pore zeolite to obtain a para-xylene depleted raffinate and a desorption effluent comprising a para-xylene enriched product, wherein the non-adsorbable gas comprises hydrogen and is non-reactive with the xylene isomers and ethylbenzene during the contacting step; and,
(b) isomerizing at least a portion of the para-xylene depleted raffinate,
wherein the sum of the partial pressures of the xylene isomers and ethylbenzene is less than the total pressure of the mixture and the gas is present in an amount sufficient to ensure that the total pressure is equal to or greater than the pressure of the isomerizing step.

46. The method of claim 45, wherein the sum is about 15% to about 99.5% of the total pressure.

47. The method of claim 45, wherein the total pressure is substantially non-decreasing.

48. The method of claim 45, wherein step (b) further comprises isomerizing the para-xylene depleted raffinate at a pressure that is equal to or less than the total pressure.

49. The method of claim 48, wherein step (b) further comprises isomerizing the para-xylene depleted raffinate at a pressure that is less than the total pressure.

50. The method of claim 45, wherein the gas is present in an amount sufficient to ensure that the total pressure is equal to or greater than an isomerization step pressure, while maintaining the partial pressure of the xylene isomers and ethylbenzene at or below the respective condensation pressures of the xylene isomers and ethylbenzene.

51. The method or claim 50, wherein the gas as present in an amount sufficient to avoid condensation of the xylene isomers.

52. The method of claim 45, wherein the gas further comprises one or more materials selected from the group consisting of argon, carbon dioxide, helium, nitrogen, methane, ethane, propane, and butane.

53. The method of claim 45, wherein the para-xylene depleted raffinate comprises meta-xylene, ortho-xylene, and hydrogen.

54. The method of claim 45, wherein step (b) further comprises isomerizing the para-xylene depleted raffinate to obtain a hydrocarbon mixture comprising equilibrated xylene isomers.

55. The method of claim 54, further comprising combining at least a portion of the xylene isomers obtained in step (b) with the mixture in step (a).

56. The method of claim 45, further comprising separating substantially pure para-xylene from the desorption effluent.

57. The method of claim 56, further comprising separating substantially pure para-xylene from the desorption effluent at a pressure that is equal to or less than the total pressure.

58. The method of claim 57, further comprising separating substantially pure para-xylene from the desorption effluent at a pressure that is less than the total pressure.

59. A method comprising the steps of:
(a) contacting a xylene isomers mixture and a non-adsorbable gas with a para-xylene selective adsorbent to obtain a para-xylene depleted raffinate comprising hydrocarbons substantially free of para-xylene and a desorption effluent comprising a para-xylene enriched product; and,
(b) isomerizing at least a portion of the para-xylene depleted raffinate,
wherein the gas comprises hydrogen and is non-reactive with the mixture during the contacting step (a), and the gas is present in an amount sufficient to provide a gas-to-hydrocarbon mole ratio in the para-xylene depleted raffinate of about 0.1:1 to about 1:1 and sufficient to ensure a raffinate pressure equal to or greater than the pressure of the isomerizing step.

60. The method of claim 59, wherein the mixture in the contacting step (a) is a gaseous mixture.

61. The method of claim 59, wherein the contacting step (a) is carried out at a substantially non-decreasing pressure.

62. The method of claim 61, further comprising separating substantially pure para-xylene from the desorption effluent.

63. The method of claim 62, further comprising separating substantially pure para-xylene from the desorption effluent at a pressure that is equal to or less than the substantially non-decreasing pressure.

64. The method of claim 63, further comprising separating substantially pure para-xylene from the desorption effluent at a pressure that is less than the substantially non-decreasing pressure.

65. The method of claim 59, wherein the gas is present in an amount sufficient to ensure a raffinate pressure equal to or greater than an isomerization step pressure, while maintaining the partial pressure of the xylene isomers and ethylbenzene at or below the respective condensation pressures of the xylene isomers and ethylbenzene.

66. The method of claim 65, wherein the gas is present in an amount sufficient to avoid condensation of the xylene isomers.

67. The method of claim 59, wherein the gas further comprises one or more materials selected from the group consisting of argon, carbon dioxide, helium, nitrogen, methane, ethane, propane, and butane.

68. The method of claim 59, wherein the para-xylene depleted raffinate comprises meta-xylene, ortho-xylene, and hydrogen.

69. The method of claim 59, wherein step (b) further comprises isomerizing the para-xylene depleted raffinate to obtain a hydrocarbon mixture comprising equilibrated xylene isomers.

70. The method of claim 69, further comprising combining at least a portion of the xylene isomers obtained in step (b) with the mixture in step (a).

* * * * *